US 12,180,454 B2

(12) United States Patent
Blanchard

(10) Patent No.: US 12,180,454 B2
(45) Date of Patent: Dec. 31, 2024

(54) AUTOMATED CELL CULTURE INCUBATOR

(71) Applicant: Thrive Bioscience, Inc., Beverly, MA (US)

(72) Inventor: Alan Blanchard, Topsfield, MA (US)

(73) Assignee: Thrive Bioscience, Inc., Beverly, MA (US)

(*) Notice: Subject to any disclaimer, the term of this patent is extended or adjusted under 35 U.S.C. 154(b) by 0 days.

(21) Appl. No.: 18/427,144

(22) Filed: Jan. 30, 2024

(65) Prior Publication Data

US 2024/0294861 A1 Sep. 5, 2024

Related U.S. Application Data

(63) Continuation of application No. 17/688,132, filed on Mar. 7, 2022, now Pat. No. 11,920,121, which is a continuation of application No. 15/563,370, filed as application No. PCT/US2016/025339 on Mar. 31, 2016, now Pat. No. 11,319,523.

(60) Provisional application No. 62/141,183, filed on Mar. 31, 2015.

(51) Int. Cl.
*C12M 1/00* (2006.01)
*C12M 1/12* (2006.01)
*C12M 1/26* (2006.01)
*C12M 1/36* (2006.01)

(52) U.S. Cl.
CPC ............ *C12M 41/14* (2013.01); *C12M 33/00* (2013.01); *C12M 37/00* (2013.01); *C12M 41/48* (2013.01)

(58) Field of Classification Search
CPC ...... C12M 41/14; C12M 41/48; C12M 33/00; C12M 37/00
See application file for complete search history.

(56) References Cited

U.S. PATENT DOCUMENTS

| | | | |
|---|---|---|---|
| 3,887,436 | A | 6/1975 | Haddad et al. |
| 4,871,676 | A | 10/1989 | Yamada |
| 5,906,943 | A | 5/1999 | Skropik et al. |
| 5,958,763 | A | 9/1999 | Goffe |
| 6,465,244 | B1 | 10/2002 | Annable et al. |

(Continued)

FOREIGN PATENT DOCUMENTS

| | | |
|---|---|---|
| CN | 101313196 A | 11/2008 |
| CN | 101501180 A | 8/2009 |

(Continued)

OTHER PUBLICATIONS

International Search Report and Written Opinion for Application No. PCT/US2016/025339 mailed Sep. 19, 2016.

(Continued)

*Primary Examiner* — Michael L Hobbs
(74) *Attorney, Agent, or Firm* — Wolf, Greenfield & Sacks, P.C.

(57) ABSTRACT

Aspects relate to an automated cell culture incubator and to methods for using such an incubator. In one aspect, the cell culture incubator includes an incubator cabinet having a transfer chamber and an internal chamber that are arranged to form an airlock configuration. In some embodiments, objects placed into the incubator cabinet are sterilized using ozone produced by an ozone generator. The incubator may include one or more transfer devices that move objects between the transfer chamber and the internal chamber.

12 Claims, 9 Drawing Sheets

(56) References Cited

U.S. PATENT DOCUMENTS

| | | |
|---|---|---|
| 7,540,844 B2 | 6/2009 | Muser |
| 8,548,745 B2 | 10/2013 | Callahan et al. |
| 9,857,360 B2 | 1/2018 | Lim |
| 10,201,896 B2 | 2/2019 | Kihara et al. |
| 10,696,937 B2 | 6/2020 | Blanchard |
| 11,034,927 B2 | 6/2021 | Blanchard |
| 11,168,297 B2 | 11/2021 | Blanchard |
| 11,319,523 B2 | 5/2022 | Blanchard |
| 11,332,705 B2 | 5/2022 | Blanchard |
| 11,879,120 B2 | 1/2024 | Blanchard |
| 11,920,121 B2 | 3/2024 | Blanchard |
| 11,920,122 B2 | 3/2024 | Blanchard |
| 2001/0039032 A1 | 11/2001 | Matsumura et al. |
| 2002/0090320 A1 | 7/2002 | Burrow et al. |
| 2002/0146347 A1 | 10/2002 | McNeil et al. |
| 2003/0040104 A1 | 2/2003 | Barbera-Guillem |
| 2004/0029266 A1 | 2/2004 | Barbera-Guillem |
| 2004/0064013 A1 | 4/2004 | Attias |
| 2004/0215362 A1* | 10/2004 | Kokubo ............... C12M 41/14 700/130 |
| 2005/0170491 A1 | 8/2005 | Takagi |
| 2005/0239040 A1 | 10/2005 | Lindenberg |
| 2005/0260743 A1 | 11/2005 | Drake et al. |
| 2006/0177922 A1* | 8/2006 | Shamah ............... B01L 9/523 435/286.2 |
| 2006/0194193 A1 | 8/2006 | Tsuruta et al. |
| 2006/0275888 A1 | 12/2006 | Hibino et al. |
| 2008/0090288 A1 | 4/2008 | Hibino et al. |
| 2010/0099177 A1 | 4/2010 | Yang et al. |
| 2010/0291619 A1 | 11/2010 | Robinson et al. |
| 2010/0330651 A1 | 12/2010 | Venter et al. |
| 2011/0027146 A1* | 2/2011 | Yokoi ............... A61L 2/208 422/292 |
| 2012/0092478 A1 | 4/2012 | Honda et al. |
| 2012/0122138 A1 | 5/2012 | Randles et al. |
| 2012/0122143 A1 | 5/2012 | Mimura et al. |
| 2012/0164721 A1 | 6/2012 | Kobayashi et al. |
| 2012/0196316 A1 | 8/2012 | Sebesta et al. |
| 2013/0074614 A1 | 3/2013 | Holmes et al. |
| 2013/0079236 A1 | 3/2013 | Holmes |
| 2013/0130361 A1 | 5/2013 | Okano et al. |
| 2013/0210130 A1 | 8/2013 | Larcher et al. |
| 2013/0273646 A1 | 10/2013 | Kobayashi et al. |
| 2013/0316442 A1 | 11/2013 | Meurville et al. |
| 2014/0051156 A1 | 2/2014 | Miyake et al. |
| 2014/0057342 A1 | 2/2014 | Uozumi et al. |
| 2014/0106386 A1 | 4/2014 | Umeno et al. |
| 2014/0106389 A1 | 4/2014 | Loewke et al. |
| 2014/0273191 A1 | 9/2014 | Tipgunlakant et al. |
| 2015/0037206 A1 | 2/2015 | Akutsu |
| 2015/0079584 A1 | 3/2015 | Gevaert et al. |
| 2015/0079621 A1 | 3/2015 | An et al. |
| 2015/0278625 A1 | 10/2015 | Finkbeiner et al. |
| 2015/0298123 A1 | 10/2015 | Block, III et al. |
| 2015/0322479 A1 | 11/2015 | Pettigrew et al. |
| 2017/0137770 A1 | 5/2017 | Sakamoto et al. |
| 2017/0361468 A1 | 12/2017 | Cheuvront et al. |
| 2018/0066218 A1 | 3/2018 | Koike et al. |
| 2018/0079999 A1 | 3/2018 | Blanchard |
| 2018/0087020 A1 | 3/2018 | Blanchard |
| 2018/0087021 A1 | 3/2018 | Blanchard |
| 2018/0346868 A1 | 12/2018 | Blanchard |
| 2020/0347339 A1 | 11/2020 | Blanchard |
| 2020/0348324 A1 | 11/2020 | Wikholm et al. |
| 2021/0222110 A1 | 7/2021 | Blanchard |
| 2021/0261903 A1 | 8/2021 | Blanchard |
| 2022/0243167 A1 | 8/2022 | Blanchard |
| 2022/0259546 A1 | 8/2022 | Blanchard |

FOREIGN PATENT DOCUMENTS

| | | |
|---|---|---|
| CN | 101987205 A | 3/2011 |
| CN | 102174395 A | 9/2011 |
| CN | 102321522 A | 1/2012 |
| CN | 102471744 A | 5/2012 |
| CN | 104245917 A | 12/2014 |
| EP | 1 460 126 A2 | 9/2004 |
| EP | 1 471 138 A1 | 10/2004 |
| EP | 1 553 166 A1 | 7/2005 |
| EP | 1 598 415 A1 | 11/2005 |
| EP | 1 650 291 A1 | 4/2006 |
| JP | 58-036383 A | 3/1983 |
| JP | H02-171866 A | 7/1990 |
| JP | 2003-052365 A | 2/2003 |
| JP | 2003-174870 A | 6/2003 |
| JP | 2004-511788 A | 4/2004 |
| JP | 2004-321111 A | 11/2004 |
| JP | 2005-102570 A | 4/2005 |
| JP | 2006-101781 A | 4/2006 |
| JP | 2006-174828 A | 7/2006 |
| JP | 2006-284288 A | 10/2006 |
| JP | 2009-511998 A | 3/2009 |
| JP | 3157029 U | 1/2010 |
| JP | 2010-154792 A | 7/2010 |
| JP | 2010-273603 A | 12/2010 |
| JP | 2011-030655 A | 2/2011 |
| JP | 2012-130297 A | 7/2012 |
| JP | 2012-524268 A | 10/2012 |
| JP | 2013-009618 A | 1/2013 |
| WO | WO 98/24883 A2 | 6/1998 |
| WO | WO 2005/009126 A1 | 2/2005 |
| WO | WO 2011/010449 A1 | 1/2011 |
| WO | WO 2011/089908 A1 | 7/2011 |
| WO | WO 2011/091333 A1 | 7/2011 |
| WO | WO 2013/016248 A1 | 1/2013 |
| WO | WO 2014/044823 A1 | 3/2014 |
| WO | WO 2012/098931 A1 | 6/2014 |
| WO | WO 2015/019595 A1 | 2/2015 |

OTHER PUBLICATIONS

International Preliminary Report on Patentability for Application No. PCT/US2016/025339 mailed Oct. 12, 2017.

Extended European Search Report for Application No. EP 16774228.7 mailed Feb. 20, 2019.

[No Author Listed] Incubator Fluorescence Microscope LCV110U Viva View FL. 2008. Brochure by Olympus America. Retrieved from the Internet:. <http://www.olympus-lifesience.com/en/microscopes/inverted/incubator/#!cms[tab]=%2Fmicroscopes%2Finverted%2Fincubator%2Fresources>.; p. 5.

[No Author Listed], Digital holographic microscopy, Wikipedia. Archived Feb. 17, 2015. Last accessed Jul. 5, 2023, from <https://web.archive.org/web/20150217070233/https://en.wikipedia.org/wiki_Digital_holographic_microscopy.htm>. 12 pages.

[No Author Listed], Nikon. BioStation IM-Q product webpage. Archived Jan. 19, 2015. Last accessed Nov. 24, 2023, from <https://web.archive.org/web/20150119025735/http://www.nikon.com/products/instruments/lineup/bioscience/time/imq/index.htm>. 11 pages.

Buggenthin et al., An automatic method for robust and fast cell detection in bright field images from high-throughput microscopy. BMC Bioinformatics. Oct. 4, 2013;14:297.

Colomb et al., Advantages of digital holographic microscopy for real-time full field absolute phase imaging. Proceedings of SPIE. Feb. 2008; 6861: 10 pages.

\* cited by examiner

AUTOMATED CELL CULTURE INCUBATOR

RELATED APPLICATIONS

This Application is a continuation of U.S. application U.S. Ser. No. 17/688,132, filed Mar. 7, 2022, entitled "Automated Cell Culture Incubator", which is a continuation of U.S. application U.S. Ser. No. 15/563,370, filed Sep. 29, 2017, entitled "Automated Cell Culture Incubator", which is a national stage filing under 35 U.S.C. § 371 of International Application No. PCT/US2016/025339, filed Mar. 31, 2016, which claims the benefit under 35 U.S.C. 119 (e) of U.S. provisional application U.S. Ser. No. 62/141,183, filed Mar. 31, 2015, and entitled "Automated Cell Culture Incubator", the entire contents of each of which are incorporated by reference herein.

FIELD

Aspects relate to cell culture incubators and to methods for using such incubators.

BACKGROUND

Cell culture incubators are used to grow and maintain cells from cell culture, which is the process by which cells are grown under controlled conditions. Cell culture vessels containing cells are stored within the incubator, which maintains conditions such as temperature and gas mixture that are suitable for cell growth. Long-term cell culture is a useful technique in both research and clinical contexts. However, maintenance of long-term cell cultures, for example, long term cultures, tissue preparations, in vitro fertilization preparations, etc., in presently available cell incubators is a laborious process requiring highly trained personnel and stringent aseptic conditions. This high level of human involvement can introduce contaminants into the culture and cause shock from environmental changes, thereby lowering culture efficiency. Accordingly, new types of cell culture incubators that provide a culture system with minimal human involvement are needed.

SUMMARY

Conventional cell culture incubators impose several barriers to productive long-term cell culture, particularly for purposes of maintaining cells for clinical purposes or for research purposes involving sensitive assays, e.g., for evaluating drug function or interrogating cellular function. For example, many presently available cell incubators require the removal of culture plates from the incubator for manipulating or viewing cells, but removing cell culture plates or other components from an incubator increases the threat of damage to the culture because upon removal, the culture is exposed to non-aseptic conditions and/or variations of the physical environment (e.g., changes in temperature, humidity, etc., or any combination thereof). Thus, the disclosure in part relates to a need for a cell culture incubator that reduces the risk of contamination and/or damage to cells by limiting exposure of the cells to contaminants, the external environment, and/or variations of the incubator environment.

According to one aspect of the disclosure, a cell culture incubator includes an incubator cabinet having a transfer chamber and an internal chamber. In some embodiments, a source of a sterilizing gas (e.g., a source of ozone gas such as an ozone generator, a source of hydrogen peroxide gas/vapor) is connected to or included in the incubator. In some embodiments, a source of sterilizing liquid (e.g., a source or dispenser of ethanol, hydrogen peroxide solutions or sodium hypochlorite solutions) is connected to or included in the incubator. In some embodiments, a sterilization gas source (e.g. an ozone generator) and one or more pumps operatively coupled with the sterilization gas source (e.g., ozone generator) are connected to or included in the incubator. The pump can be configured for supplying ozone gas to the transfer chamber, the internal chamber, or both. The pump can also be configured for removing sterilization gas (e.g., ozone gas) from the transfer chamber, the internal chamber, or both.

In some embodiments, the cell culture incubator also includes an external door opening from an external environment to the transfer chamber, a transfer chamber door opening from the transfer chamber to the internal chamber, and a transfer device for moving one or more items between the transfer chamber and the internal chamber. In some embodiments, the internal chamber is configured to hold a plurality of cell culture vessels (e.g. flasks, suspension culture flasks, spinner flasks, plates, petri dishes and bags) and/or other items (e.g., one or more supplies such as disposable supplies required for cell manipulation, for example, pipette tips). In some embodiments, the sterilization medium generator is in fluid communication with the transfer and/or internal chamber. In some embodiments, the external door forms a substantially gas-tight seal when closed. In some embodiments, the transfer chamber is configured to hold a plurality of cell culture vessels (e.g. flasks, plates, petri dishes and bags) and/or other items (e.g., one or more supplies such as disposable supplies required for cell manipulation, for example, pipette tips).

In some embodiments, the incubator further comprises a controller for controlling operation of the transfer device for moving one or more items into, within or out from the incubator. In some embodiments, the controller is located exterior to the incubator cabinet. In some embodiments, the controller comprises a computer. In some embodiments, the incubator further comprises a cell culture vessel transfer device for moving one or more cell culture vessels within the internal chamber. In some embodiments, the cell culture vessel transfer device comprises one or more robotic elements.

In some embodiments, one or more pumps are configured to remove the ozone gas or other gaseous sterilizing agent from the incubator cabinet. In some embodiments, one or more reversible pumps are provided that are configured to both supply and remove gas (depending on mode of operation) from the transfer chamber and/or internal chamber. In some embodiments, an incubator includes a decomposition catalyst (e.g., in the transfer chamber) to accelerate breakdown of a sterilizing gas and help remove it safely from the internal chamber. Non-limiting examples of decomposition catalysts include $MnO_2$, $NiO_2$, charcoal, etc., or a combination thereof.

In some embodiments, the incubator further comprises a monitoring system. In some embodiments, the monitoring system monitors the addition and/or removal of a sterilizing agent to or from the transfer chamber and/or the internal chamber. In some embodiments, the monitoring system monitors the temperature, humidity, gas (e.g. $O_2$, $CO_2$, $N_2$, etc.) concentration within the transfer chamber and/or the internal chamber. In some embodiments, the monitoring system comprises probes and/or sensors. In some embodiments, the probes and/or sensors are located in the internal chamber and/or transfer chamber of the incubator. In some embodiments, the probes and/or sensors are electronically connected to a display panel, e.g., present on the exterior of the incubator cabinet. In some embodiments, one or more controllers are attached to the sensors and other systems to control the internal environment of the incubator based on the sensed incubator conditions.

In some embodiments, the incubator further comprises a fluid filtration system. In some embodiments, the fluid filtration system filters gas or vapor that is entering and/or exiting the incubator. A fluid filtration system can be a liquid filter and/or a gas (e.g., air, ozone, etc.) filter. In some embodiments, the fluid filtration system filters liquids entering and/or exiting the incubator. In some embodiments, the fluid filtration system is a sterilizing filter (e.g. a UV filter sterilizer or heat sterilizer).

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
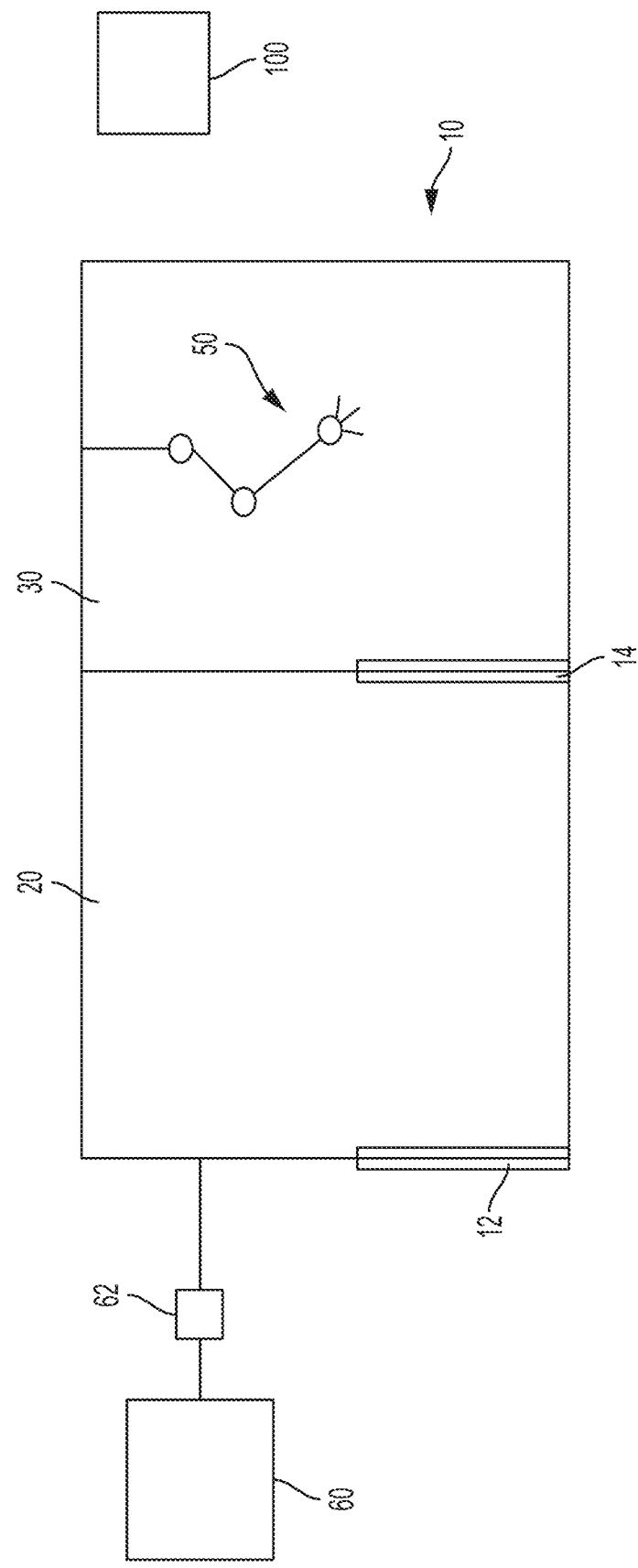
FIG. 1 is a schematic of an illustrative embodiment of a cell culture incubator having an incubator cabinet with a transfer chamber and an internal chamber according to one embodiment.

Aspects of the disclosure relate to automated incubators that enable productive long-term cell culture. It has been appreciated that, when items from the external environment are inserted into a cell culture incubator, such items may bring along contaminants that may contaminate the cells held inside the incubator. Furthermore, it has been recognized that there is a need for a cell culture incubator that reduces exposure of cells to contaminants. It has also been appreciated that, each time the door to a conventional single-chamber cell culture incubator is opened, the internal conditions (e.g., temperature, gas mixture, and/or humidity) are changed due to exposure to the external environment. It takes time for the incubator to adjust back to desirable levels. In the meantime, the cells held within the incubator are subjected to fluctuating conditions, which may negatively affect the health or activity of the cells. It has been recognized that there is a need for a cell culture incubator that reduces the amount of condition fluctuations that cells are subjected to when items are moved in and out of an incubator.

According to one aspect, a cell culture incubator includes an airlock arrangement that permits items to be transferred from an external environment into an internal chamber of the cell culture incubator while helping to maintain the conditions and/or sterility of the internal chamber.

In some embodiments, the cell culture incubator may include an incubator cabinet with a transfer chamber and an internal chamber. The transfer chamber serves as an intermediate space in which items can be sterilized before entering the internal chamber and/or conditions can be equilibrated with the internal chamber before communication with the internal chamber is opened. The cell culture incubator may include at least two doors to create an airlock arrangement. In some embodiments, an external door is configured to open and close to permit communication between the transfer chamber and the external environment. In some embodiments, an internal door is configured to open and close to permit communication between the transfer chamber and the internal chamber. Operation of the external and/or internal doors may be provided in an automated fashion.

In some embodiments, a door is an element that permits communication between two or more environments or regions when opened and prevents communication between the two or more environments or regions when closed. A door may be of any type, such as a sliding door, pocket door, swinging door, hinged door, revolving door, pivot door, or folding door. The door may be manually, mechanically, or electrically operated. For example, an operator may open or close a door by manually grasping, pulling, pushing, and/or otherwise physically interacting with the door or an element thereof (e.g., a handle) or by operating a mechanical control (e.g., a button, toggle, spin-wheel, key, switch, cursor, screw, dial, screen, or touch-screen). In certain embodiments, a door may be controlled by electrical or digital controls, such as by a computer. A door may be an automatically opening door. For example, a door may include a sensor, such as a pressure, infrared, motion, or remote sensor, that detects whether the door is open or closed and/or controls when the door opens or closes. A door may open by mechanical, pneumatic, electrical, or other means. In some embodiments, one or more doors may include one or more locking mechanisms. In particular environments, one or more doors may include one or more interlocks (e.g., a mechanical interlock such as a pin, bar, or lock or an electrical interlock such as a switch) to prevent one or more doors from opening at an undesirable time (e.g., when one or more chambers are open to the outside environment).

The airlock arrangement may be used to help decrease exposure of the internal chamber to the external environment, or exposure of the external environment to the internal chamber. In some embodiments, to utilize the airlock arrangement, one door is opened at a time. For example, an operator may open the external door to gain access to the transfer chamber. The operator may then insert item(s) such as pipette tips into the transfer chamber. An operator may operate the external door by directly manipulating the door. However, in some embodiments, an operator may operate the door indirectly by controlling the operation of the door remotely, e.g., through the use of automation configured to control opening and closing of the doors. In some embodiments, the transfer chamber door remains closed while the external door is open. In some embodiments, after item(s) are inserted into the transfer chamber, the external door is closed (e.g., directly or indirectly by an operator). Once the external door is closed, a sterilization process inside the transfer chamber is used to sterilize the inserted item(s). Once sterilization is complete, the internal door is opened and the sterilized items are moved from the transfer chamber into the internal chamber (e.g., by one or more transfer devices).

An illustrative example of how the transfer chamber helps to preserve the internal conditions of the internal chamber will now be described. When the transfer chamber is opened to the external environment, the internal chamber remains closed such that there is no communication between the external environment and the internal chamber. Once the transfer chamber is closed to the external environment, sensors inside the transfer chamber detect one or more internal conditions associated with the transfer chamber, such as temperature, humidity, gas content, air pressure, light, etc. The conditions within the transfer chamber are then adjusted (e.g., by raising/lowering the temperature, increasing/decreasing humidity, etc.) to become closer to or substantially match those of the internal chamber. Once the internal conditions between the transfer chamber and the internal chamber are sufficiently similar, the internal chamber opens to the transfer chamber. Items from the transfer chamber can then be moved into the internal chamber. With the conditions in the transfer chamber being close to or substantially matching those in the internal chamber, the conditions of the internal chamber are not subjected to significant fluctuations when the internal door is opened (e.g., when items are moved from the transfer chamber to the internal chamber).

In some embodiments, the environment inside an incubator is controlled by a control system that may be configured to control the temperature, humidity, carbon dioxide, oxygen and other gaseous components (e.g., sterilization gases, such as, ozone, and hydrogen peroxide) inside the incubator (e.g., in one or more internal chambers). In some embodiments, a control system controls the environmental conditions (e.g., temperature, humidity, carbon dioxide, oxygen and other gaseous components) within each internal chamber separately. For example, in order to protect sensitive mechanical, electronic and optical components, the humidity of an internal chamber may be maintained at a lower level than an internal chamber (e.g., a level in a range of 30% to under 70% relative humidity). In some embodiments, the incubator is further provided with a monitoring system with predefined sensors. Examples of monitoring devices include but are not limited to oxygen monitors, carbon dioxide monitors, ozone gas detectors, hydrogen peroxide monitors and multi gas monitors. For example, in some embodiments, an incubator includes a plurality of sensors responsive to different parameters relevant to cell growth, which may include temperature, air purity, contaminant levels, pH, humidity, $N_2$, $CO_2$, $O_2$ and light. By means of this monitoring system, parameters in the incubator can be measured using sensors for the duration of a culture or process. In some embodiments, parameters measured by the sensors are transmitted by the monitoring system via a line to a computer-controlled monitoring and control system for further processing as discussed elsewhere herein.

In some embodiments, an environmental monitoring system can be used in conjunction with an incubator described herein. In some embodiments, one or more sensors that provide for the measurement of temperature, air composition (e.g., $CO_2$ concentration, $O_2$ concentration, etc.), and/or humidity of the system can be associated with an incubator (e.g., fitted within an incubator cabinet). In some embodiments, one or more such sensors can be incorporated as part of an incubator (e.g., attached to, integral to, or otherwise connected to an internal wall or door of the incubator). In some cases, one or more sensors can be positioned at any suitable location(s) outside or inside an incubator cabinet (e.g., within a transfer chamber and/or an internal chamber, for example attached to an internal wall, and/or upper or lower internal surface).

In some embodiments, a gas sensor is provided that can provide a reading in real time of the concentration of gas in contact with the sensor (e.g., gas in a cabinet, or ambient air) in percent, parts per million, or any other standard unit. Gas sensors for use in the methods and incubators provided herein include $CO_2$ sensors, $O_2$ sensors, $N_2$ sensors, ozone gas detectors, hydrogen peroxide monitors, multi gas monitors, and CO sensors. Such sensors are available from a number of commercial sources. In some cases, the environment of the incubator may be modulated or controlled based upon the information provided by the sensors described herein. For example, the level of $CO_2$ in an incubator may be increased upon indication from a $CO_2$ sensor that a lower than desirable concentration of $CO_2$ is present in the incubator.

In some embodiments, one or more heating or cooling elements can be incorporated within the incubator (e.g., on an inner surface of the cabinet or door, and/or integrated within one or more of the walls and/or the base of the cabinet) for purposes of controlling the temperature within the incubator. In some embodiments, a heating element can be used for thawing liquids, for example, cell culture media or other reagents. In some embodiments, one or more air or oxygen sources, carbon filters, and/or one or more humidification or dehumidification systems are connected to the incubator and configured to control the level of oxygen, carbon dioxide, and/or humidity within the incubator (e.g., in response to signals from the one or more sensors in or attached to the incubator).

In some embodiments, the incubator further comprises a fluid filtration system. Generally, fluid filtration systems are used to filter gas or vapor that is entering and/or exiting the incubator. For example, a fluid filtration system may sterilize the air entering the incubator from the exterior environment, or sterilize the air exiting the incubator prior to being released into the exterior environment. Liquid filtration systems are also contemplated herein. Non-limiting examples of fluid filtration systems include air filters, carbon filters and sterilizing filters (e.g. a UV filter sterilizer or heat sterilizer).

In some embodiments, one or more controllers are attached to the sensors and other systems to control the internal environment of the incubator.

In some embodiments, an incubator can include one or more light sources (e.g., an incandescent bulb, LED, UV, or other light source). These can be placed within the incubator to illuminate regions within the cabinet. In some embodiments, the culture system operation is monitored using a camera or other light sensitive device that can be placed within or outside the incubator. In some embodiments, the light source is a sterilizing light source. For example, a UV lamp may be located within the transfer chamber and/or the interior chamber of the incubator provided herein.

In some embodiments, the incubator includes a transparent object (e.g., window) that allows visible light or other light wavelengths from within the incubator to be detected by a camera or other light sensitive device placed outside the incubator. In some embodiments, the inner surface of the transparent object can be wiped (e.g., from the inside of the cabinet) to prevent or remove condensation droplets that may accumulate (e.g., due to the humid air inside the incubator) on the inner surface and interfere with the monitoring of the system. In some embodiments, the surface can be wiped by a wiper that is automatically controlled by a controller.

In some embodiments, mechanical or electrical controls may be used to open one or more doors. In certain embodiments, an interlock arrangement is included such that only one door may be opened at a time, for example, to prevent contamination of an internal chamber by exposure to the external environment. In some embodiments, the airlock arrangement prevents the contents of the incubator from entering the external environment. For example, the airlock arrangement may prevent the release of biohazardous agents that are being cultured in the incubator. An operator may open (e.g., mechanically or by activating an electrical or digital control) the external door to gain access to the transfer chamber (e.g., to insert a pipette tip). During the time that the external door is open, the interlock may prevent the internal door from opening. After the external door is closed (e.g., mechanically or by activation of an electrical or digital control), the internal door may be opened (e.g., to transfer the pipette tip from the transfer chamber to an internal chamber).

The transfer chamber may be of any appropriate size and geometry and may be made of any suitable material. In some embodiments, a transfer chamber may include one or more plastics, polymers, metals, or glasses.

The internal chamber may include one or more windows (e.g., optical windows made of glass, plastic, composite, or other substantially transparent material for viewing an area inside the incubator cabinet). The internal chamber may be of any appropriate size and geometry. In some embodiments, an incubator cabinet may include more than one internal chamber. In other embodiments, an internal chamber may include one or more partitions to define different regions of an internal chamber. One or more internal chambers or partitions thereof may have different environmental conditions. The environment (e.g., air pressure, gas content, temperature, light, and humidity) inside an internal chamber may be measured and/or controlled by one or more meters, monitors, sensors, controls, pumps, valves, apertures, and/or light sources.

An internal chamber may be made of any useful material. In some embodiments, an internal chamber may include one or more plastics, polymers, metals, or glasses.

In some embodiments, the transfer chamber and/or the internal chamber may have a gas-tight or hermetic seal, e.g., around one or more windows or doors. In particular embodiments, sealants such as grease and/or mechanical elements such as o-rings, gaskets, septa, KF, LF, QF, quick coupling, or other sealing mechanisms may be used to establish one or more gas-tight seals. In some embodiments, grooves, depressions, protrusions, and/or molded plastic elements may facilitate in establishing one or more gas-tight seals.

In some embodiments, an incubator (e.g., an internal chamber, and/or a transfer chamber of an incubator cabinet) includes one or more windows and/or doors, that, when closed, are sealed to preserve sterility (e.g., after one or more chambers of the incubator have been sterilized). In some embodiments, each seal of the incubator is air tight up to a threshold level of pressure (e.g., up to 1 atm). In some embodiments, a gasket is provided to ensure a desired level of sealing capacity. In general, a "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoroethylene). It is often desirable that a gasket be made from a material that provides some degree of yielding such that it is able to deform and fill tightly the space it is designed for, including any slight irregularities. In some embodiments, gaskets can be used with an application of sealant directly to the gasket surface to function properly. In some embodiments, a gasket material can be a closed-cell neoprene foam which is non-reactant with carbon dioxide or ozone.

In some embodiments, a pressure test may be used to detect leaks in the internal chamber and/or the transfer chamber. In one illustrative example of a pressure test, pressurized air is delivered into a chamber and the pressure level inside the chamber is measured. A dropping pressure level may indicate a leak. For example, to test the internal chamber for leaks, pressurized air is delivered into the internal chamber with the internal door closed. A pressure sensor in the internal chamber measures pressure levels. If the pressure does not increase inside the internal chamber as pressurized air is delivered and/or if pressure levels drop once pressurized air delivery is stopped, such a condition may indicate a leak.

In some embodiments, the cell culture system further comprises a sterilization medium supply (e.g., an ozone generator) coupled to a pump, wherein the sterilization medium supply (e.g., the ozone generator) is configured for supplying sterilization medium (e.g., ozone gas) to the transfer chamber. In some embodiments, the sterilization medium supply (e.g., ozone generator) is configured for supplying sterilization medium (e.g., ozone gas) to the one or more internal chambers.

As discussed above, a sterilization process may be used to sterilize items that have been placed into the internal chamber. In some embodiments, the sterilization process uses ozone to sterilize the items. In some embodiments, the ozone is stored as a compressed gas source. The compressed ozone source can be located exterior to the incubator or within the incubator. The cell culture incubator may include an ozone generator that produces and introduce ozone gas into the incubator. In some embodiments, the ozone generator is positioned outside of the incubator cabinet, and is in fluid communication with the incubator cabinet via one or more ports into the transfer chamber and appropriate fluid conduits (e.g., tubing such as—Teflon, viton, polycarbonate, polyurethane, or other ozone-compatible tubing). One or more valves, flow meters, ozone sensors, pumps, or other devices may control the amount of ozone introduced to one or more portions of the incubator cabinet and/or be used to remove excess ozone from the incubator cabinet.

The ozone generator may operate by converting oxygen gas from ambient air into ozone gas e.g., by means of a coronal discharge, ultraviolet light, dielectric barrier discharge, or electrolysis. An ozone generator for use in conjunction with an incubator provided herein may be of any useful type, size, or geometry. In some embodiments, an incubator includes both an incubator cabinet and an ozone generator. The ozone generator may be positioned outside the incubator cabinet or may be positioned inside the incubator cabinet. Ozone gas produced by the ozone generator may be introduced into the incubator cabinet or portion thereof (e.g., a transfer chamber or an internal chamber) by means of tubing (e.g., Teflon, viton, polycarbonate, polyurethane, or other ozone-compatible tubing) and one or more ports. One or more valves, flow meters, ozone sensors, pumps, or other mechanisms may control the amount of ozone introduced to one or more portions of the incubator cabinet and/or be used to remove excess ozone from the incubator cabinet or portion thereof. In some embodiments, one or more ozone sensors may provide information to an interlock system to prevent the inner door from being opened if ozone is present at a detectable level (or above a threshold level that can be specified) in the transfer chamber. This can be useful to prevent ozone from entering the internal chamber.

In some embodiments, the sterilization process uses hydrogen peroxide gas or hydrogen peroxide vapor to sterilize the items. In some embodiments, the hydrogen peroxide vapor is stored as a compressed gas source and distributed as a low pressure, dry vapor. A hydrogen peroxide vapor generator for use in conjunction with an incubator provided herein may be of any useful type, size, or geometry. In some embodiments, an incubator includes both an incubator cabinet and a hydrogen peroxide vapor generator. The hydrogen peroxide vapor generator may be positioned outside the incubator cabinet or may be positioned inside the incubator cabinet. Hydrogen peroxide vapor produced by the hydrogen peroxide vapor generator may be introduced into the incubator cabinet or portion thereof (e.g., a transfer chamber or an internal chamber) by means of tubing (e.g., Teflon, viton, polycarbonate, polyurethane, or other ozone-compatible tubing) and one or more ports. One or more valves, flow meters, hydrogen peroxide vapor sensors, pumps, or other mechanisms may control the amount of hydrogen peroxide vapor introduced to one or more portions of the incubator cabinet and/or be used to remove excess hydrogen peroxide vapor from the incubator cabinet or portion thereof. In some embodiments, one or more hydrogen peroxide vapor sensors may provide information to an interlock system to prevent the inner door from being opened if hydrogen peroxide vapor is present at a detectable level (or above a threshold level that can be specified) in the transfer chamber. This can be useful to prevent hydrogen peroxide vapor from entering the internal chamber.

The sterilization process may be used to sterilize not only items that are inserted into the incubator, but may be used to sterilize the chamber(s) of the incubator, such as in a cleaning cycle. In some embodiments, the incubator is emptied of cells and other items that would be harmed by a sterilization process. In one embodiment, a cleaning cycle entails applying 100 ppm ozone at 37° C. and 80% for 15 minutes. In some cases, the transfer chamber alone may be sterilized while the internal door is closed. In other embodiments, the internal chamber alone is sterilized while the internal door is closed. In yet other embodiments, the internal chamber may be sterilized by opening the internal door or by routing sterilization medium (e.g., ozone or other gas) directly into the internal chamber.

It should be appreciated that other sterilization mediums and processes other than ozone can be used. For example, items may be sterilized using other types of chemical sterilization, steam, heat, radiation, or any other suitable type of sterilization.

A transfer device for moving one or more items may be used to move items between the transfer chamber and the internal chamber. In some embodiments, the transfer device includes a conveyor belt or other similar device for maneuvering items. In some embodiments, more than one transfer device may be included. In some embodiments, one or more transfer devices are located in the transfer chamber and/or in the internal chamber. In some embodiments, a transfer device may include one or more robotic elements. For example, a transfer device may include one or more robotic arms capable of gripping, lifting, pushing, grabbing, sliding, rotating, translating, releasing, raising, lowering, and/or tilting one or more items (e.g., pipettes).

In some embodiments, a transfer device selectively and/or releasably grips one or more pipettes or cell culture vessels or other items. In certain embodiments, a transfer device may include an arm coupled to a mechanical gripper. For example, an arm may include a mechanical gripper at or near one end for releasably gripping a pipette and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more items (e.g., pipettes or vessels) at different horizontal and vertical positions within an incubator (e.g., within a storage array located in an internal chamber).

The transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements.

As used herein, a "transfer device for moving one or more items" refers to a device that can transfer one or more items from a first location to a second location. In some embodiments, the one or more items are one or more cell culture vessels. In other embodiments, the one or more items are useful for maintenance of one or more cell culture vessels and include, but are not limited to, pipettes, capillaries, liquids (e.g., cell culture medium), nutrients, and other materials. In certain embodiments, the transfer device may transfer one or more items to or from multiple locations in an incubator. For example, a transfer device may be used to move a pipette to a maintenance location in an internal chamber for maintenance of one or more cell culture vessels. In some embodiments, an incubator includes more than one transfer device for moving one or more items (e.g., two or more separate transfer devices for transferring items between and within chambers).

In some embodiments, a transfer device includes a device that can transfer one or more cell culture vessels from a first location to a second location. In certain embodiments, the transfer device may transfer one or more items to or from multiple locations in an incubator. For example, a cell culture vessel transfer device may be used to move a cell culture vessel from a transfer chamber to an internal chamber, and/or from a storage location to an imaging location. In some embodiments, an incubator includes more than one cell culture vessel transfer device for moving one or more items (e.g., two or more separate cell culture vessel transfer devices for transferring cell culture vessels between and within chambers). A cell culture vessel transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a cell culture vessel transfer device may include one or more robotic elements. For example, a cell culture vessel transfer device may include a robotic arm capable of gripping, lifting, pushing, grabbing, sliding, rotating, translating, releasing, raising, lowering, and/or tilting one or more cell culture vessels. In preferred embodiments, the cell culture vessel transfer device selectively and releasably grips one or more cell culture vessels. In certain embodiments, a cell culture vessel transfer device may include an arm coupled to a mechanical gripper. For example, an arm may include a mechanical gripper at or near one end for releasably gripping a cell culture vessel and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessels at different horizontal and vertical positions within an incubator (e.g., within a storage array in an internal chamber).

In some embodiments, a transfer device comprises a robotic arm. In some embodiments, the robotic arm includes a platform within an incubator cabinet that may move along a rail or conveyor running in various directions along an inner surface (e.g., inner wall, base, etc.) of incubator cabinet. In some embodiments, an incubator cabinet may be configured with more than one (e.g., 2, 3, 4, or 5, or more) robotic arms to increase the throughput of the instrument and to provide redundancy in the event that one of the robotic arms fail.

In some embodiments, a transfer device further includes a gripper assembly coupled to a robotic arm. In some embodiments, the gripper assembly includes one or more grippers mounted on the end of the robotic arm, each gripper having two or more (e.g., 3, 4, 5, or more) gripper fingers. In some embodiments, each of the gripper fingers on the robotic arm has a groove, friction plate, rubber pad, or other gripping surface. The gripping surface can allow the fingers to grip and transport various types of containers (e.g., culture vessels) within the cabinets. In some embodiments, the robotic arm may have an absolute encoder either coupled to the gripper assembly, or the platform, or a separate absolute encoder for each of the gripper assembly and/or the platform to determine whether the robotic arm is in a position where it may be safely homed (e.g., returned to a resting or storage configuration and/or location or origin of an operational coordinate system) without hitting an obstruction.

In some embodiments, because it may be desirable in certain situations for the reach of the robotic arm not to extend to some areas of the incubator cabinet, the robotic arm may instead reach these locations by inserting a container into or removing a container from a shuttle or conveyor belt located, for example on the incubator cabinet floor or other surface that moves along an axis (e.g., x-axis, y-axis) and provides access to at least some of those locations to which the robotic arm cannot reach.

In some embodiments, an incubator cabinet is designed to be used in conjunction with an external assay or laboratory automation system. For example, in some embodiments, the incubator cabinet may have a door having an opening large enough to allow the gripper arm to pivot outside of the incubator cabinet with a sufficient reach for the fingers to transport culture vessels or other containers or components between a transport line of the laboratory automation system and the incubator cabinet or the external assay components and the incubator cabinet.

In some embodiments, a robotic arm is designed to carry, among other things, culture vessels, in which case movements of the robotic arm are controlled to prevent jerking or accelerations of such vessels or other movements which may cause the spilling of samples from the vessels. In some embodiments, a robotic arm is designed to carry, among other things, culture vessels, in which case movements of the robotic arm are controlled to prevent movement of such vessels in ways which cause newly plated cells to congregate/concentrate in specific areas of the culture vessel.

In some embodiments, because a robotic arm transports vessels or other containers between specific positions in the incubator cabinet, the robotic arm or other components of the incubator can be designed to track precisely where the vessels or other containers are located. In some case, in an incubator cabinet with which a robotic arm may be used, there are likely to be areas, such as where other components of the incubator cabinet or walls of the incubator cabinet are located, and thus where certain movements of the robotic arm may be limited. In these cases, a homing mechanism can be used for each of various motors of the arms (e.g., x-motor, theta-motor and z-motor) to properly position the robotic arm to a known location after it is powered up or if a robotic arm collides with another object before resuming operation.

In some embodiments, an uninterruptible power supply ("UPS") is attached to or within the incubator cabinet, or contained with it, to allow for an orderly shut-down of incubator operations, including saving of various automation and sample information and the completion of any transport or transfer process that is underway (e.g., the transport of a container or vessel that is being carried by the robotic arm to its destination). The operator may be alerted to unauthorized opening of the incubator by an audible signal, a visual signal, an electronic signal (e.g., an email or a text message), or in some other manner. e.g. In some embodiments, a sensor or other feature is provided to detect when one or more doors of an incubator are opened (e.g., when an incubator cabinet door, such as an external or internal door, is opened). Such features are useful because they allow operators to keep track of or be warned of any unscheduled or unauthorized openings of the incubator (e.g., the incubator cabinet) that could jeopardize sterility, spoil a production, compromise an assay or experiment, etc.

In some embodiments, a radiofrequency beacon or other signal source is located within the incubator (e.g., within the incubator cabinet) that can be used to determine the location of one or more devices within the incubator cabinet (e.g., devices having sensors that can detect the signal and use it to determine their location). In some embodiments, the devices could have signal sources and the sensor(s) could be located within one or more of the chambers of an incubator cabinet (e.g., located on an internal surface of an internal chamber).

In some embodiments, light signals or lasers (e.g., a grid of laser signals) can be used to determine the location of one or more devices or components within the incubator cabinet. Such information can be communicated, e.g., wired or wirelessly, to an external computer or monitoring station. The information can be used to control operation of a transfer device, e.g., a robotic arm, within the incubator cabinet to ensure that the transfer device can grab, manipulate or maneuver devices or items appropriately within the incubator cabinet.

In some embodiments, before containers or vessels are brought into an incubator cabinet, a user can select an automation system protocol based on the particular containers, vessels, ingredients, or cells that are being inserted into the incubator cabinet. Relevant information related to the incubator and/or one or more incubator components, and the cells being grown can be entered into a data system. For example, one or more identifiers such as barcodes (e.g., 1D or 2D barcodes) can be placed on the container or vessel, and other significant information, such as, the type of container, the contents of the container, what assays or manipulations are to be performed on the sample in the container can be specified. In some embodiments, information related to the incubator system and/or cells can be contained in one or more barcodes, on a separate data system, or a combination thereof. The user may also enter information that identifies the dimensionality (e.g., height, diameter) of the vessel or other container or the system itself can be configured to determine the height or other dimensions of the vessel or other container. Using this information, the robotic arm may be requested to transport a particular container, such as when an analytical module is ready to perform an assay or other manipulation on cells grown in the vessels or has completed performing an assay or manipulation.

The incubators provided herein include several components, including sensors, environmental control systems, robotics, etc. which may operate together at the direction of a computer, processor, microcontroller or other controller. The components may include, for example, a transfer device (e.g., robotic arm), a liquid handling devices, a delivery system for delivering culture vessels, or other components to or from the incubator cabinet, an environmental control system for controlling the temperature and other environmental aspects of the incubator cabinet, a door operation system, an imaging or detection system, and a cell culture assay system.

In some cases, operations such as controlling operations of a cell culture incubator and/or components provided therein or interfacing therewith may be implemented using hardware, software, or a combination thereof. When implemented in software, the software code can be executed on any suitable processor or collection of processors, whether provided in a single component or distributed among multiple components. Such processors may be implemented as integrated circuits, with one or more processors in an integrated circuit component. A processor may be implemented using circuitry in any suitable format.

A computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile or fixed electronic device, including the incubator itself.

In some cases, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. In other examples, a computer may receive input information through speech recognition or in other audible format, through visible gestures, through haptic input (e.g., including vibrations, tactile and/or other forces), or any combination thereof.

One or more computers may be interconnected by one or more networks in any suitable form, including as a local area network or a wide area network, such as an enterprise network or the Internet. Such networks may be based on any suitable technology and may operate according to any suitable protocol and may include wireless networks, wired networks, or fiber optic networks.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible storage medium) encoded with one or more programs that, when executed on one or more computers or other processors, perform methods that implement the various methods or processes described herein.

In some embodiments, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the methods or processes described herein. As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computer or other processor to implement various aspects of the methods or processes described herein. Additionally, it should be appreciated that according to one aspect of this embodiment, one or more programs that when executed perform a method or process described herein need not reside on a single computer or processor, but may be distributed in a modular fashion amongst a number of different computers or processors to implement various procedures or operations.

Executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. Non-limiting examples of data storage include structured, unstructured, localized, distributed, short-term and/or long term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, or located within the incubator but outside the incubator cabinet), and can be stored in computer-readable media to provide information about conditions during a cell culture incubation. In some embodiments, the readable media comprises a database. In some embodiments, said database contains data from a single incubator. In some embodiments, said database contains data from a plurality of incubators. In some embodiments, data is stored in a manner that makes it tamper-proof. In some embodiments, all data generated by the instrument (e.g., an incubator) is stored. In some embodiments, a subset of data is stored.

In some embodiments, the component (e.g., a computer) controls various processes performed inside the incubator. For example, a computer may direct control equipment (e.g., a manipulator, an imager, a fluid handling system, etc.). In some embodiments, the computer controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

Turning to the figures, FIG. 1 depicts one illustrative embodiment of a cell culture incubator 1. The cell culture incubator includes an incubator cabinet 10 having a transfer chamber 20 and an internal chamber 30. An external door 12 opens and closes to permit communication between the transfer chamber 20 and the external environment (e.g. the environment external to the incubator cabinet 10). A transfer chamber door 14 opens and closes to permit communication between the transfer chamber 20 and the internal chamber 30.

The transfer chamber 20 and/or the internal chamber 30 may include one or more sensors for determining various internal conditions such as, but not limited to, temperature, humidity, gas content, pressure, and light levels. The transfer chamber 20 and/or the internal chamber 30 may include components for adjusting such internal conditions, such as a heater, humidifier, gas generator, air pump, etc.

In some embodiments, a transfer device is positioned within the internal chamber 30. In other embodiments, the transfer device is positioned within the transfer chamber 20. In yet other embodiments, the transfer device is positioned in both the transfer chamber and the internal chamber. In other embodiments, the transfer device can freely move between the chambers (such as with a robot that can move between the chambers).

In the illustrative embodiment shown in FIG. 1, a transfer device 50 moves one or more items between the transfer chamber 20 and the internal chamber 30. The transfer device 50 may reach into transfer chamber 20, pick up one or more items from the transfer chamber 20, and move the item(s) into the internal chamber 30. The transfer device 50 may be a robotic arm or any other suitable transfer device described herein.

Figure 8:
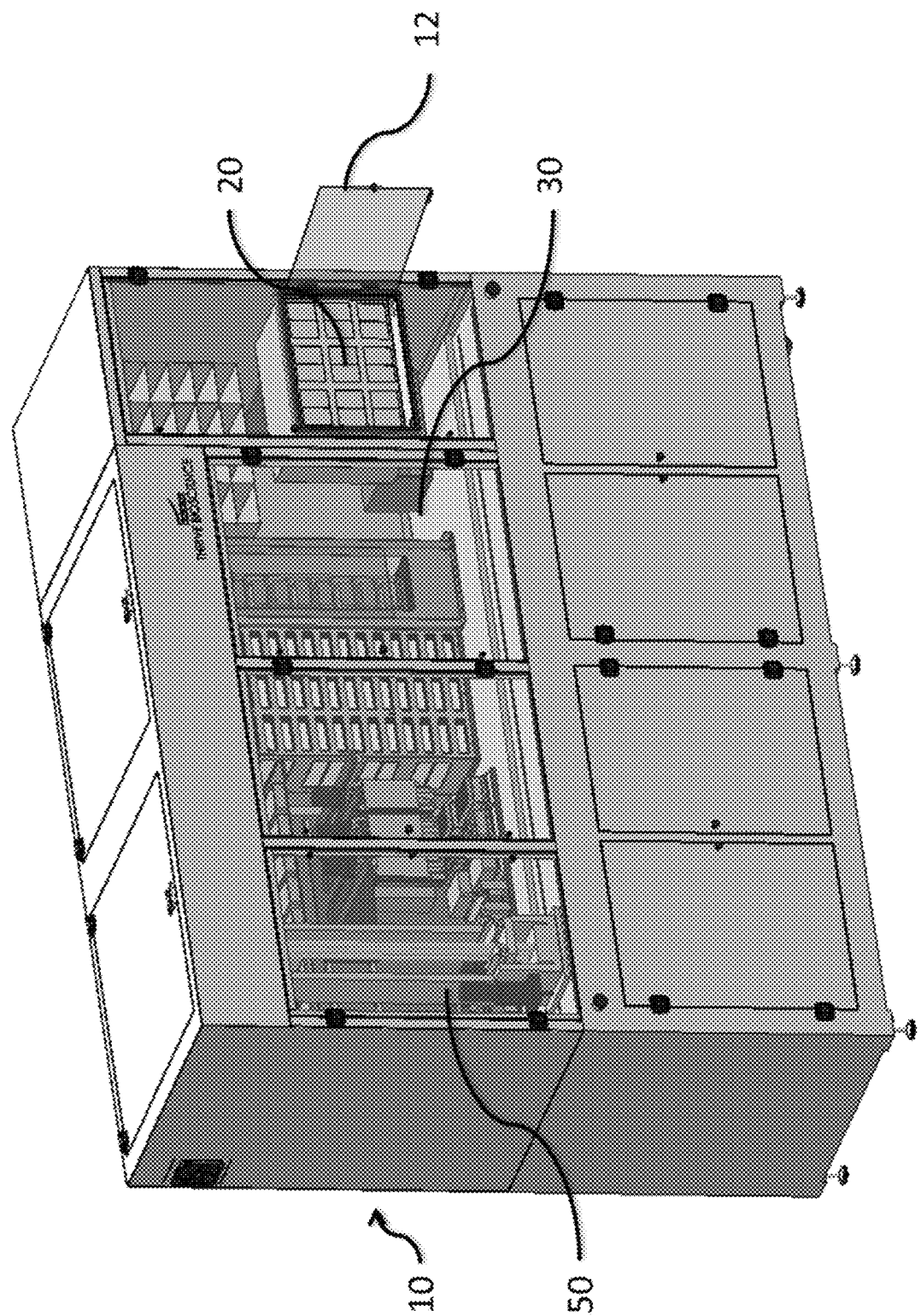
FIG. 8 is a schematic of an illustrative embodiment of a cell culture incubator having an incubator cabinet with a transfer chamber and an internal chamber according to one embodiment.

In an additional illustrative embodiment shown in FIG. 8, a transfer device 50 moves one or more items between the transfer chamber 20 and the internal chamber 30. The transfer device 50 may reach into transfer chamber 20, pick up one or more items from the transfer chamber 20, and move the item(s) into the internal chamber 30. The transfer device 50 may be a robotic arm or any other suitable transfer device described herein.

Figure 2:
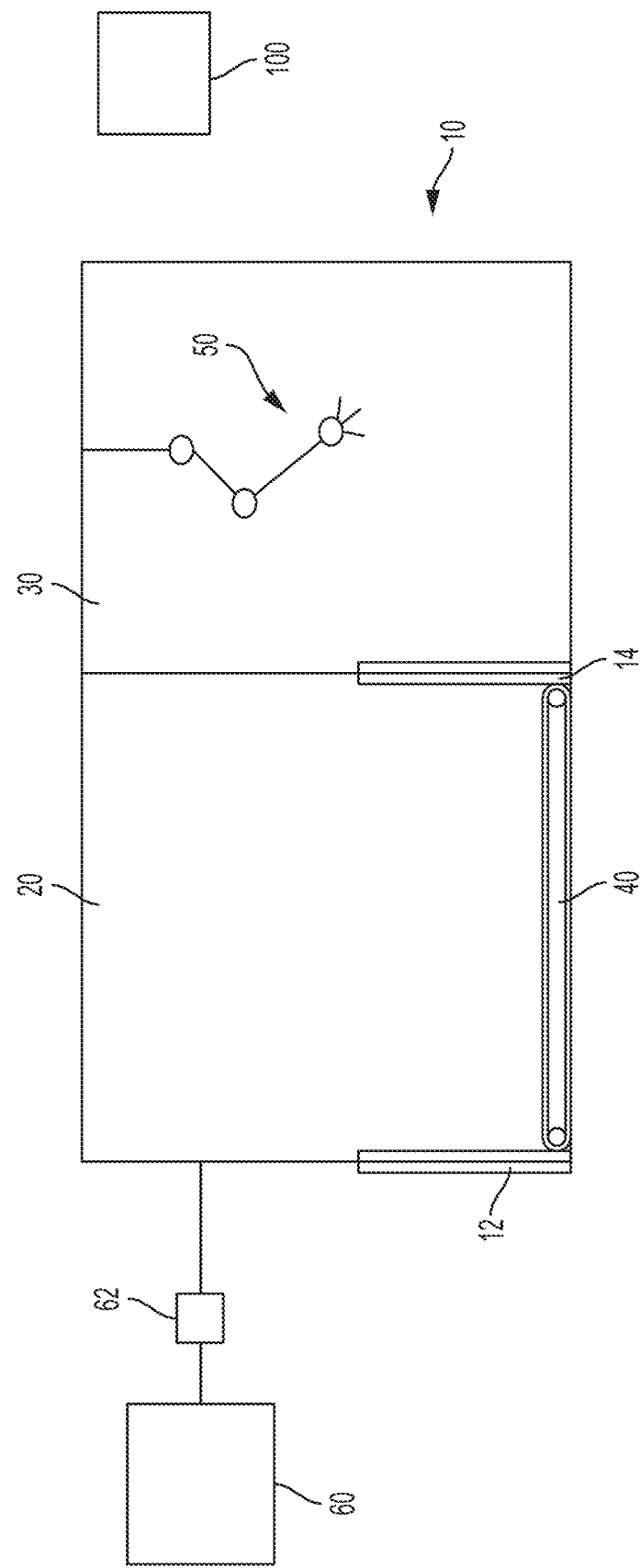
FIG. 2 is a schematic of an illustrative embodiment of a cell culture incubator having a transfer device in a transfer chamber according to one embodiment.

In some embodiments, more than one transfer device may be included in the cell culture incubator cabinet. In the illustrative embodiment shown in FIG. 2, in addition to the transfer device 50 of the internal chamber 30, a transfer device 40 is included in the transfer chamber 20. The transfer device 40 is a belt conveyor system that conveys items from one end of the transfer chamber 20 to the other end of the transfer chamber 20. As one illustrative example, a user opens external door 12 and places an item on the transfer device 40. The transfer device 40 conveys the item towards transfer chamber door 14, which opens to receive the item. A robotic arm 50 of the internal chamber 30 may move the item off the transfer device 40 and move the item to an appropriate location in the internal chamber 30. Alternatively, the item falls off the conveyor 40 as it approaches the end of the conveyor and lands in internal chamber 30. The item may be moved within the internal chamber 30 by a robotic arm 50 or other transfer device.

In some embodiments, one or more components in an incubator cabinet and/or one a transfer device may be used to locate and/or align the transfer device. In some embodiments, a location or alignment component may be a physical feature (e.g., one or more protrusions, indentations, guides, etc., or any combination thereof). In some embodiments, a location or alignment component may be a signal and/or sensor (e.g., a laser, a camera, an ultrasonic range finder, etc., or any combination thereof).

It should be appreciated that other types of transfer devices may be used as part of the cell culture incubator. In one illustrative embodiment shown in FIG. 5, the cell culture incubator 1 includes a transfer device 70 that includes a linearly actuated receptacle. As shown in more detail in FIG. 6, the transfer device 70 includes a housing 76 and a receptacle 78 that is translated through housing 76 via an actuator 79. The actuator 79 moves the receptacle 78 from the first end 71 of the device to the second end 73 of the device. The receptacle 78 can extend at least partially through a first opening 72 at the first end 71 of the transfer device 70 and through a second hole 74 at the second end 73 of the device.

Figure 5:
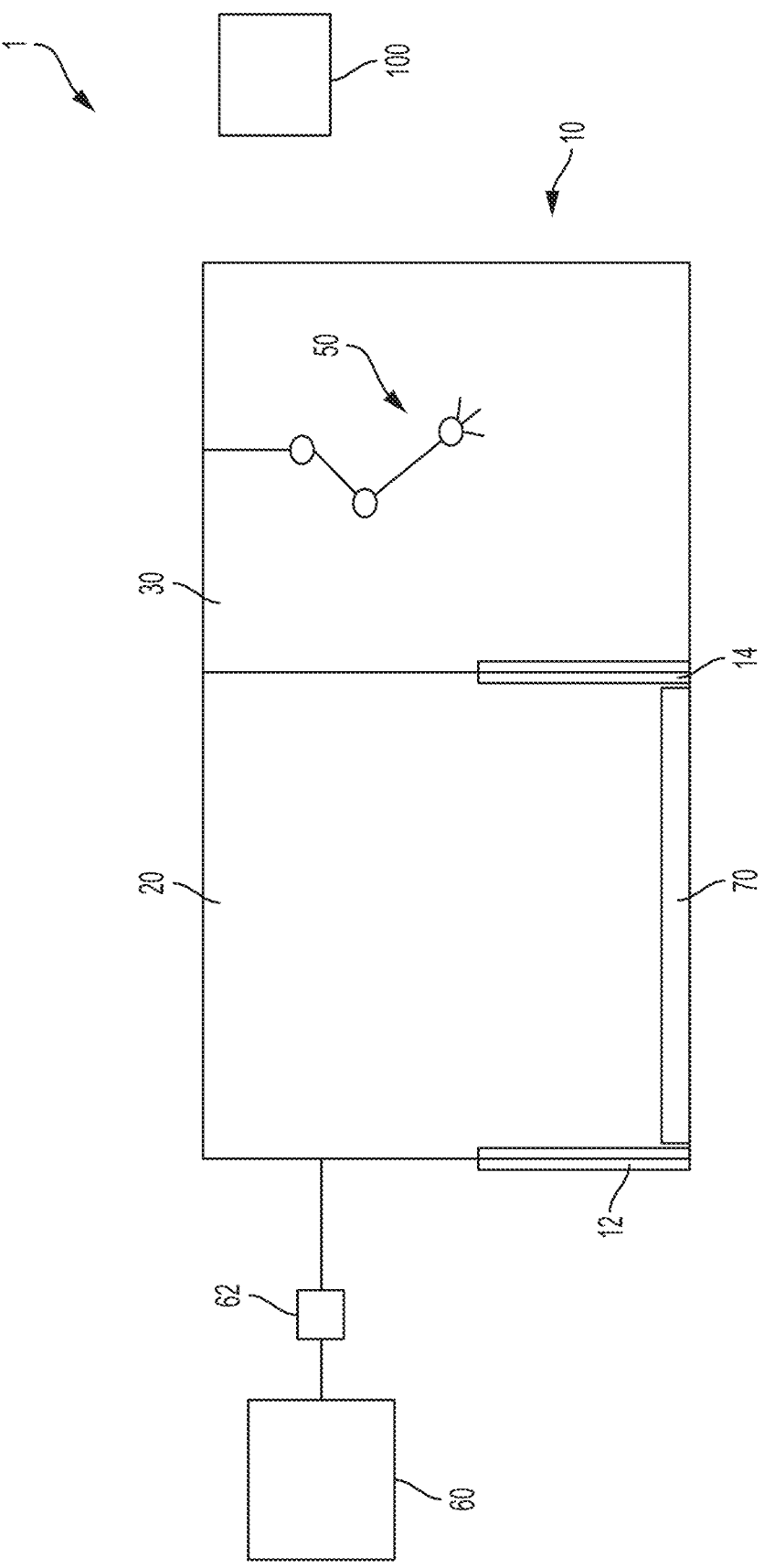
FIG. 5 is a schematic of an illustrative embodiment of a cell culture incubator having a linearly translating transfer device according to one embodiment.
Figure 6:
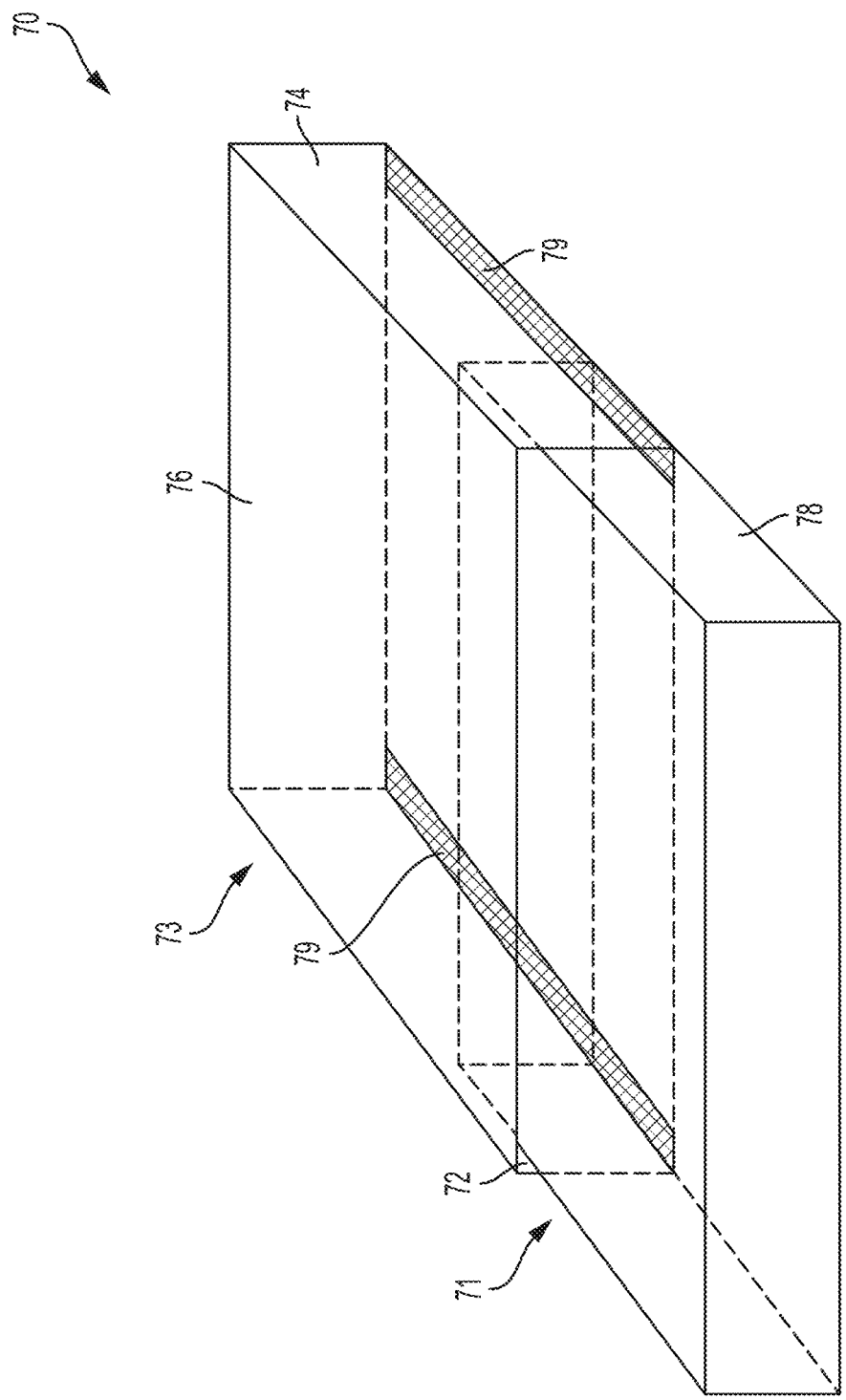
FIG. 6 is a perspective view of the transfer device shown in FIG. 5.

One illustrative example involving an operation of transfer device 70 will now be discussed in reference to FIGS. 5-6. First, a user opens the external door 12. The actuator 79 of the transfer device 70 moves receptacle 78 out through the first opening 72 so that a user can place one or more items into the receptacle 78. The user places any desired items into the receptacle 78 through an open top or through an opening of the receptacle. A user may then indicate to the transfer device 70 that all desired items have been placed into the receptacle 78 by pushing a button, pushing the receptacle 78 toward the second end 73, or otherwise providing a signal to the transfer device 70. The actuator 79 then moves the receptacle 78 back into the housing 76 toward the second end 73. Once the receptacle 78 has been retracted into the housing 76, the external door 12 is closed. Once the external door 12 is closed, and any appropriate sterilization and/or condition equilibration processes inside transfer chamber 20 are completed, the internal door 14 is opened. The actuator 79 of the transfer device 70 moves the receptacle 78 at least partially through the second opening 74. In some cases, the receptacle 78 may be moved at least partially into the internal chamber 30. The transfer device 50 of the internal chamber picks up the item(s) in the receptacle 78 and places the item(s) in an appropriate location in the internal chamber 30.

Figure 7:
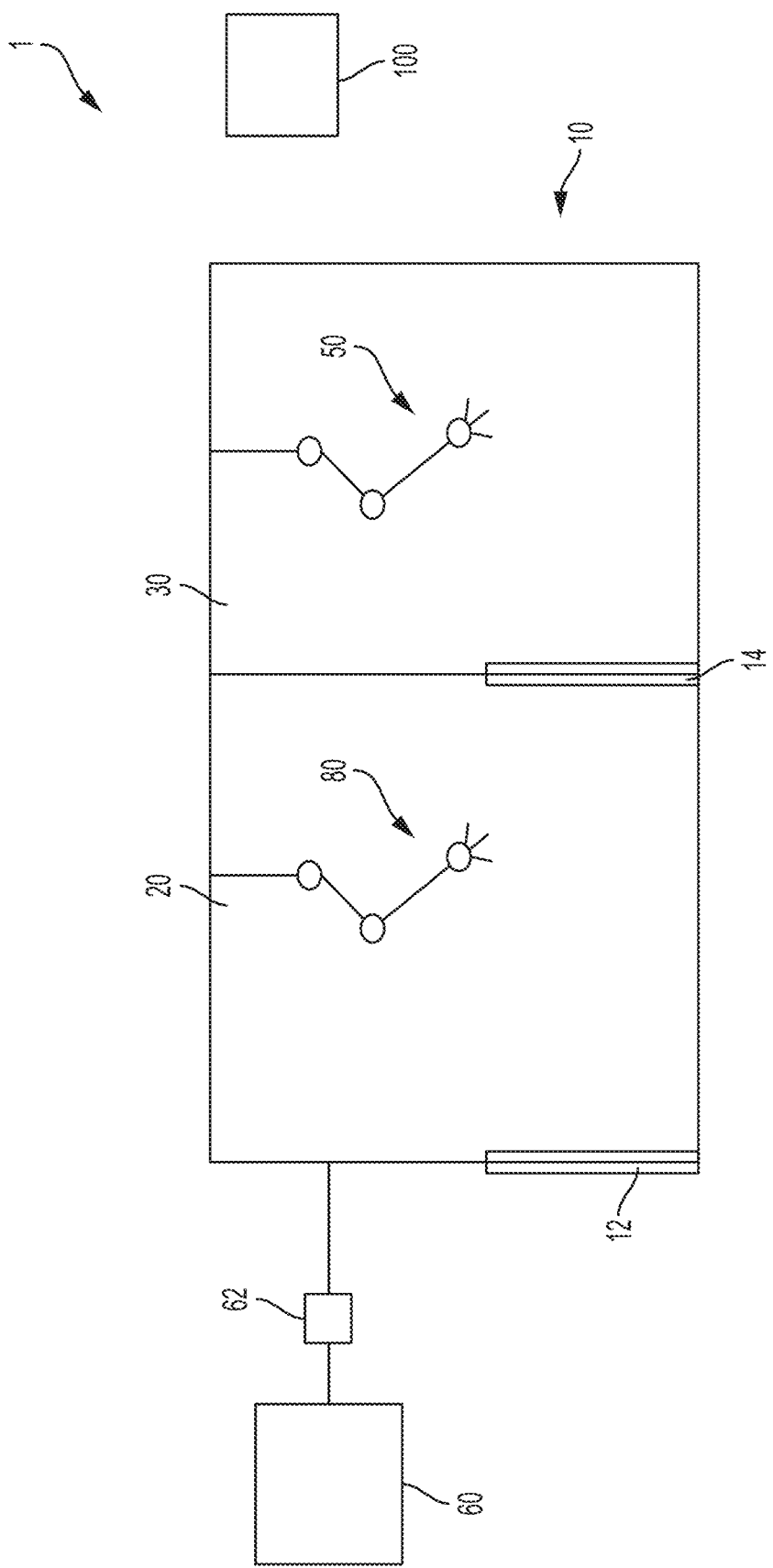
FIG. 7 is a schematic of an illustrative embodiment of a cell culture incubator having a robotic arm in the transfer chamber according to one embodiment.

In yet another illustrative embodiment, shown in FIG. 7, the transfer chamber 20 includes a transfer device 80 that is a robotic arm type transfer device. It should be appreciated that any number and any type of transfer devices may be included in an incubator (e.g., within one or more chambers of an incubator cabinet).

As described herein, a sterilization process may occur within transfer chamber 20 to sterilize any items added into the transfer chamber 20 from the external environment. In one embodiment, a sterilization medium is used as part of the sterilization process. As seen in FIG. 1, a sterilization medium source 60 is in fluid communication with the transfer chamber 20. A pump 62 may be used to convey sterilization medium from the sterilization medium source 60 to the transfer chamber 20. Alternatively or in addition, the pump 62 may move sterilization medium from the transfer chamber 20 to the sterilization medium source 60. It should be appreciated that pump 62 may be integrated with the source 60 itself. In some embodiments, no pump is included at all.

In one embodiment, the sterilization medium used is ozone. However, it should be appreciated that other types of sterilization medium and corresponding source may be used other than ozone. As such, sterilization medium source 60 may be a source of any suitable sterilization medium.

The sterilization medium provided to the transfer chamber may be used to sterilize the incubator cabinet or other parts of the incubator as part of a cleaning cycle. In one embodiment, during a cleaning cycle, sterilization medium provided by the source 60 is provided into the transfer chamber 20 to sterilize the chamber itself. The internal door 14 may remain closed to prohibit sterilization medium from entering internal chamber 30.

In another embodiment, both the transfer chamber 20 and the internal chamber 30 are sterilized. During a cleaning cycle, the internal door 14 may be opened while ozone gas or other sterilization medium is generated or provided from source 60. With the internal door 14 open, sterilization medium may enter into both transfer chamber 20 and internal chamber 30.

Figure 3:
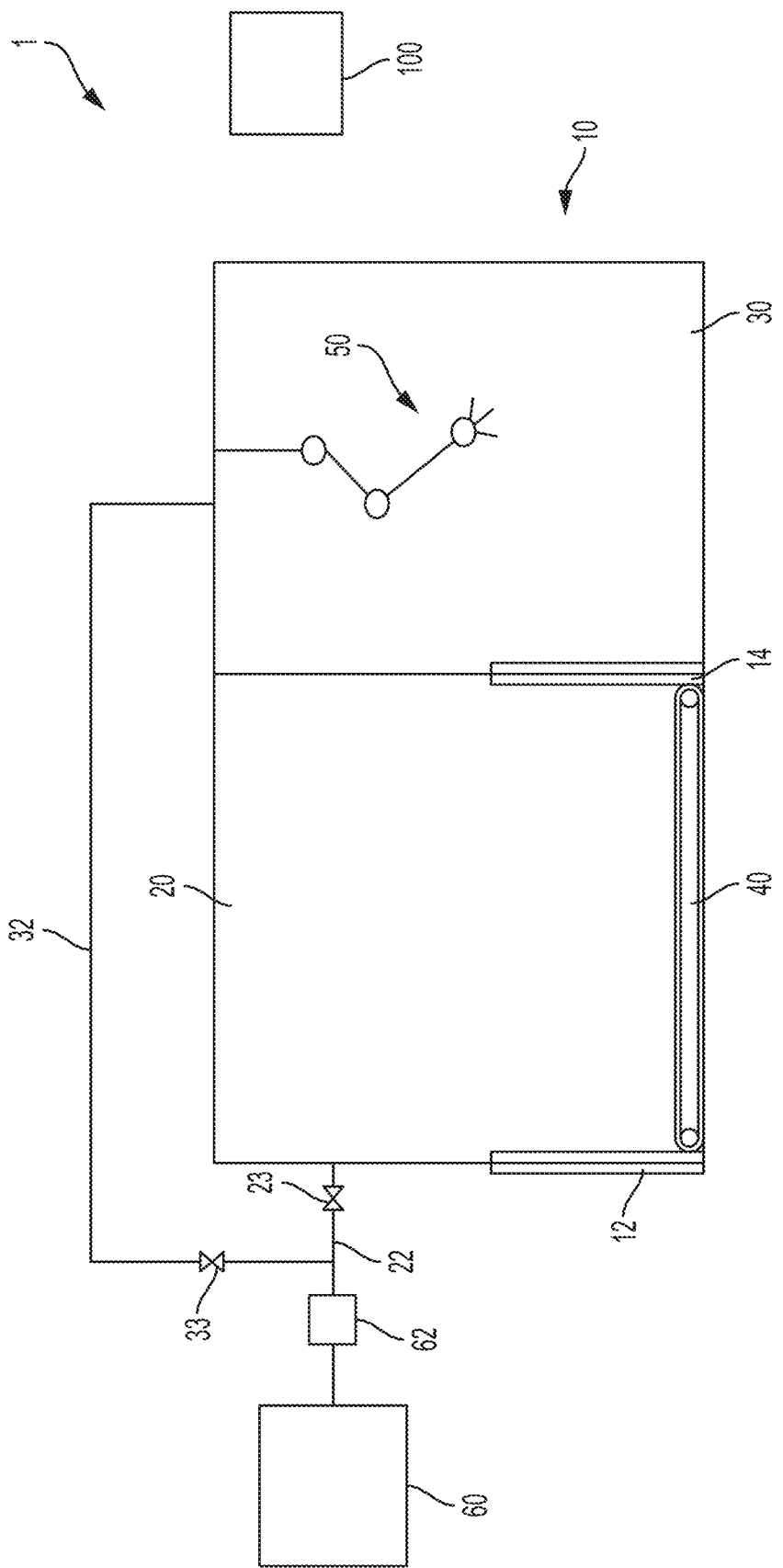
FIG. 3 is a schematic of an illustrative embodiment of a cell culture incubator having an ozone flow system according to one embodiment.

In one illustrative embodiment, shown in FIG. 3, sterilization medium may be directly routed to internal chamber 30. The sterilization medium flow path includes one or more flow controllers 23, 33 (such as valves) to control the sterilization medium flow path. Flow controller 23 controls flow through a transfer chamber path 22 and flow controller 33 controls flow through an internal chamber path 32. In one mode, where sterilization medium is desired only in the transfer chamber 20, flow controller 33 is closed while flow controller 23 is open, and the external door 12 and internal door 14 are closed. In another mode, where sterilization medium is desired only in the internal chamber, flow controller 23 is closed while flow controller 33 is open, and internal door 14 is closed. In yet another mode, where sterilization medium is desired in both chambers, both flow controllers 23, 33 are open while external door 12 is closed. Internal door 14 may be open or closed.

Figure 4:
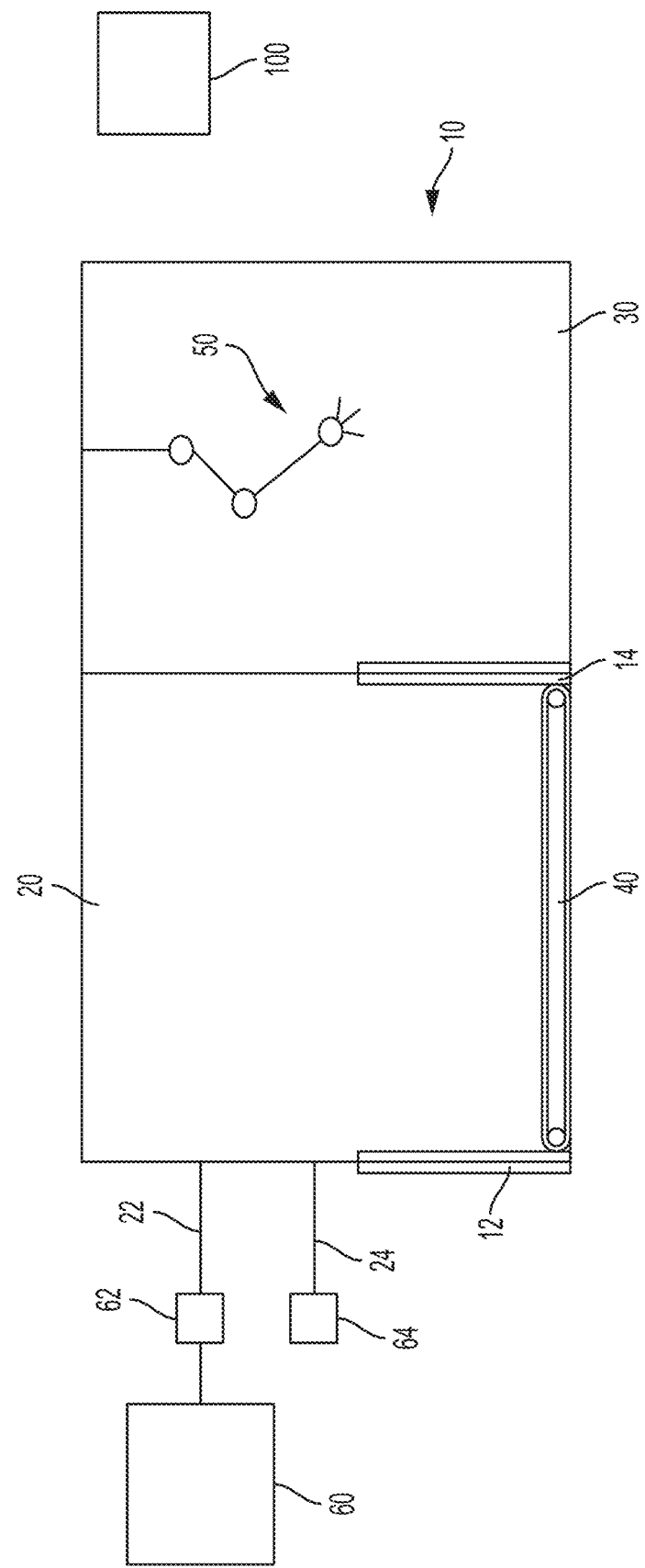
FIG. 4 is a schematic of an illustrative embodiment of a cell culture incubator having a second pump according to one embodiment.

In some embodiments, as seen in FIG. 4, a second pump 64 is included to remove ozone gas and/or other fluids from the transfer chamber 20 through an exit path 24.

Figure 9:
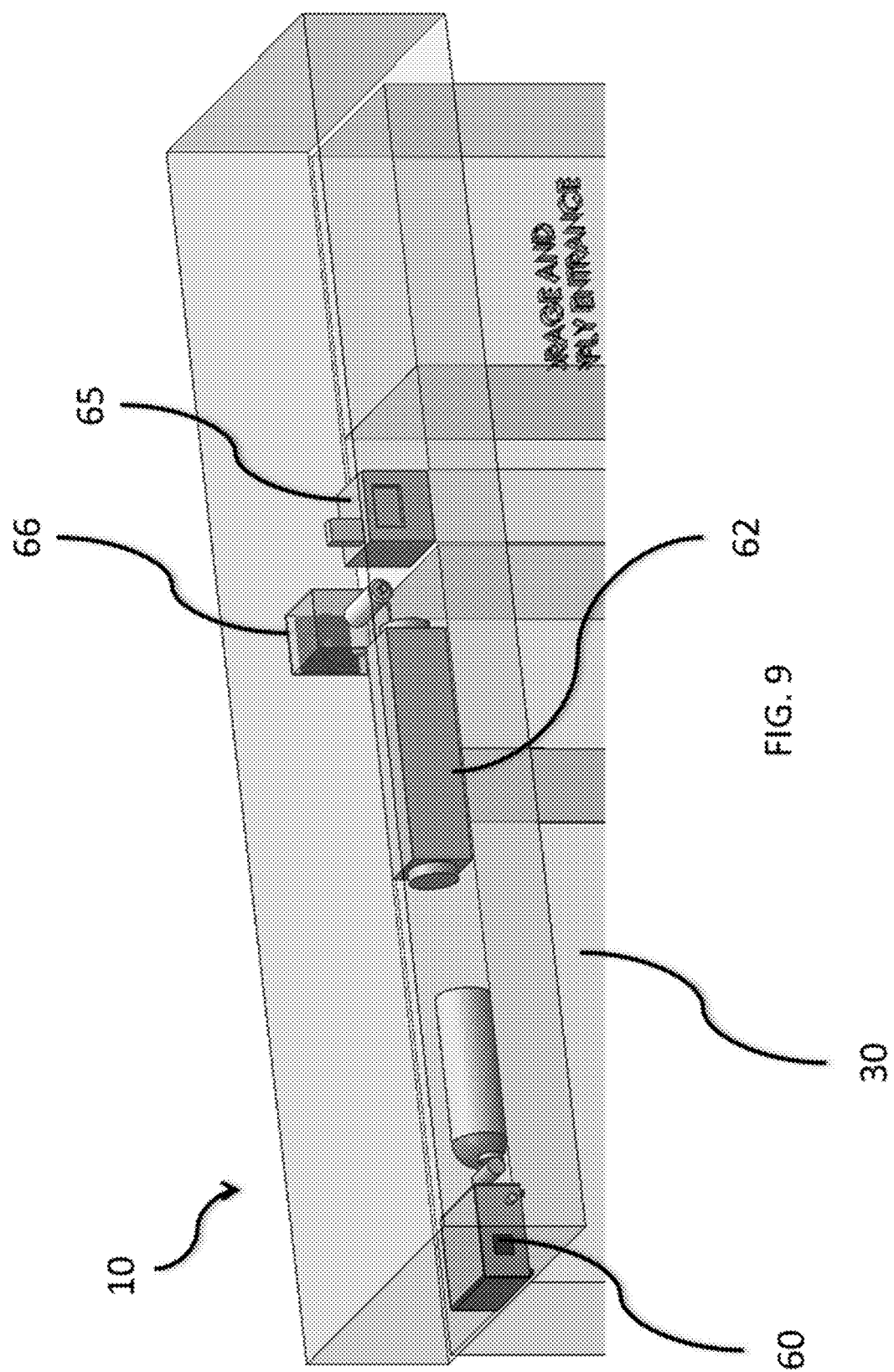
FIG. 9 is a schematic of an illustrative embodiment of a cell culture incubator having an ozone flow system according to one embodiment.

In one illustrative embodiment, shown in FIG. 9, sterilization medium may be directly routed to internal chamber 30. A pump 62 may be used to convey sterilization medium from the sterilization medium source 60 to the internal chamber 30. The controller may receive information from one or more sensors 65 located inside the incubator cabinet 10 (sensors may be in the transfer chamber 20 and/or the internal chamber 30), or from one or more sensors 66 located on the exterior of the incubator cabinet 10. The controller may communicate with one or more components of the cell culture incubator 1 and/or the sensors via wireless signals and/or wired signals.

In some embodiments, a controller 100 may be used to control one or more components of the cell culture incubator 1. For example, the controller 100 may control the sterilization medium source 60, pump 62 and/or 64, external door 12, internal door 14, transfer device 40, 50 and/or 70, sensors, and any components that affect the internal conditions of the incubator (e.g., heaters, humidifiers, gas generators, etc.). The controller 100 may be external to the incubator cabinet, as seen in FIG. 1. The controller may receive information from one or more sensors located inside the incubator cabinet 10 (sensors may be in the transfer chamber 20 and/or the internal chamber 30). The controller may communicate with one or more components of the cell culture incubator 1 and/or the sensors via wireless signals and/or wired signals.

Automated Cell Culture

Aspects of the disclosure relate to incubators and methods for culturing, manipulating, and/or monitoring cells under controlled conditions (e.g., under aseptic and/or sterile conditions). In some aspects, incubators and methods include automated components. In some aspects, incubators and methods are useful for long term cell culture (e.g., to grow and maintain cells for recombinant protein expression or to grow and/or differentiate cells for therapeutic applications such as implantation). In some embodiments, cell cultures are grown within a culture vessel in an incubator of the disclosure.

Culture Vessel

As used herein, a "cell culture vessel" is a device including a housing and one or more chambers for culturing cells. In some embodiments, the housing is a frame. The frame may be coupled to a lid. The one or more chambers may include cell culturing media including one or more membranes. In some embodiments, a cell culture vessel may include nutrients for promoting the growth of cells. In certain embodiments, a cell culture vessel may entirely enclose one or more cells or groups thereof. The housing of a cell culture vessel may include one or more pores or openings to permit the transfer of gases between a cell culture vessel and its surrounding environment. In certain embodiments, a cell culture vessel includes a transparent or optically clear window. For example, a lid coupled to the housing of a cell culture vessel may include an optically clear portion for viewing cells e.g., with a microscope or other imager. In some embodiments, a cell culture vessel includes one or more portions that are substantially non-reflective.

Cell culture vessels may be configured for culturing cells of different types, including eukaryotic or prokaryotic cells. In some embodiments, cells are mammalian cells (e.g., human cells, canine cells, bovine cells, ovine cells, feline cells, or rodent cells such as rabbit, mouse, or rat cells). In some embodiments, cells are insect cells, avian cells, microbial cells (e.g., yeast cells such as *Saccharomyces cerevisiae, Kluyveromyces lactis,* or *Pischia pastoris* cells, or bacterial cells such as *Escherichia coli, Bacillus subtilis,* or *Corynebacterium* cells), insect cells (e.g., *Drosophila* cells, or Sf9 or Sf21 cells), plant cells (e.g., algal cells) or cells of any other type.

In some embodiments, cell culture vessels may be pre-kitted with one or more reagents desired for a particular purpose, e.g., for growing cells, for differentiating cells, for subjecting cells to a particular assay condition, etc. In some embodiments, pre-kitted cell culture vessels contain reagents useful for performing a particular experiment (e.g., cell growth media, growth factors, selection agents, labeling agents, etc.) on a cell culture, in advance of the experiment. Pre-kitted cell culture vessels may facilitate experimental protocols by providing cell culture-ready vessels that do not require the addition of reagents. For example, progenitor cells from a patient may be added to a cell culture vessel pre-kitted with reagents for cell differentiation for the purpose of expanding a population of differentiated cells for autologous cell therapy. Pre-kitted cell culture vessels can be stored at any appropriate temperature, which is determined by the recommended storage parameters of the reagents within the pre-kitted cell culture vessel. In some embodiments, pre-kitted cell culture storage vessels are stored prior to use at temperatures between about −80° C. and about 37° C. In some embodiments, pre-kitted cell culture storage vessels are stored prior to use at temperatures between about −80° C. and about −20° C. In some embodiments, pre-kitted cell culture storage vessels are stored prior to use at temperatures between about −20° C. and about 4° C. In some embodiments, pre-kitted cell culture storage vessels are stored prior to use at temperatures between about 4° C. and about 37° C. In some embodiments, pre-kitted cell culture vessels are disposable. In some embodiments, pre-kitted cell culture vessels are reusable and/or refillable.

In some embodiments, cells are cultured for producing natural products (e.g., taxols, pigments, fatty acids, biofuels, etc.). In some embodiments, cells are cultured to express recombinant products (e.g., recombinant protein products such as antibodies, hormones, growth factors, or other therapeutic peptides or proteins). In some embodiments, cells are expanded and/or differentiated for therapeutic use such as implantation into a subject (e.g., a human subject) in order to provide or supplement a cellular, tissue, or organ function that is missing or defective in the subject.

In some embodiments, cells are from immortalized cell lines. Non-limiting examples of cell lines include human cells, for example, HeLa cells, prostate cancer cells (e.g., DU145, PC3 and/or Lncap cells), breast cancer cells (e.g., MCF-7, MDA-MB-438, and/or T47D cells), acute myeloid leukemia cells (e.g., THP-1 cells), glioblastoma cells (e.g., U87 cells), neuroblastoma cells (e.g., SHSY5Y cells), bone cancer cells (e.g., Saos-2 cells), and chronic myelogenous leukemia cells (e.g., KBM-7 cells). In some embodiments, cell lines include primate cell lines, rodent cell lines (e.g., rat or mouse cell lines), canine cell lines, feline cell lines, Zebrafish cell lines, Xenopus cell lines, plant cell lines, or any other cell lines. In some embodiments, cells are human 293 cells (e.g., 293-T or HEK 293 cells), murine 3T3 cells, Chinese hamster ovary (CHO) cells, CML TI cells, or Jurkat cells.

In some embodiments, cells are primary cells, feeder cells, or stem cells. In some embodiments, cells are isolated from a subject (e.g., a human subject). In some embodiments, cells are primary cells isolated from a tissue or a biopsy sample. In some embodiments, cells are hematopoietic cells. In some embodiments, cells are stem cells, e.g., embryonic stem cells, mesenchymal stem cells, cancer stem cells, etc. In some embodiments, cells are isolated from a tissue or organ (e.g., a human tissue or organ), including but not limited to, solid tissues and organs. In some embodiments, cells can be isolated from placenta, umbilical cord, bone marrow, liver, blood, including cord blood, or any other suitable tissue. In some embodiments, patient-specific cells are isolated from a patient for culture (e.g., for cell expansion and optionally differentiation) and subsequent re-implantation into the same patient or into a different patient. Accordingly, in some embodiments, cells grown in the incubators disclosed herein may be used for allogenic or autogeneic therapy. In some embodiments, cells grown in the incubators disclosed herein may be genetically modified, expanded and reintroduced into a patient for the purpose of providing an immunotherapy (e.g., chimeric antigen receptor therapy (CAR-T), or delivery of CRISPR/Cas modified cells).

In some embodiments, a primary cell culture includes epithelial cells (e.g., corneal epithelial cells, mammary epithelial cells, etc.), fibroblasts, myoblasts (e.g., human skeletal myoblasts), keratinocytes, endothelial cells (e.g., microvascular endothelial cells), neural cells, smooth muscle cells, hematopoietic cells, placental cells, or a combination of two or more thereof.

In some embodiments, cells are recombinant cells (e.g., hybridoma cells or cells that express one or more recombinant products). In some embodiments, cells are infected with one or more viruses.

Primary Cell Isolation

In some embodiments, cells are isolated from tissues or biological samples for ex vivo culture in the incubators provided herein. In some embodiments, cells (e.g., white blood cells) are isolated from blood. In some embodiments, cells are released from tissues or biological samples using physical and/or enzymatic disruption. In some embodiments, one or more enzymes such as collagenase, trypsin, or pronase are used to digest the extracellular matrix. In some embodiments, tissue or biological samples are placed in culture medium (e.g., with or without physical or enzymatic disruption), and cells that are released and that grow in the culture medium can be isolated for further culture.

Cell Culture

As used herein, cell culture refers to a procedure for maintaining and/or growing cells under controlled conditions (e.g., ex vivo). In some embodiments, cells are cultured under conditions to promote cell growth and replication, conditions to promote expression of a recombinant product, conditions to promote differentiation (e.g., into one or more tissue specific cell types), or a combination of two or more thereof.

In some embodiments, cell culture vessels are configured for culturing cells in suspension. In some embodiments, cell culture vessels are configured for culturing adherent cells. In some embodiments, cell culture vessels are configured for 2D or 3D cell culture. In some embodiments, cell culture vessels include one or more surfaces or micro-carriers to support cell growth. In some embodiments, these are coated with extracellular matrix components (e.g., collagen, fibrin, and/or laminin components) to increase adhesion properties and provide other signals needed for growth and differentiation. In some embodiments, cell culture vessels include one or more synthetic hydrogels such as polyacrylamide or polyethylene glycol (PEG) gels to support cell growth. In some embodiments, cell culture vessels include a solid support with embedded nutrients (e.g., a gel or agar, for example, for certain bacterial or yeast cultures). In some embodiments, cell culture vessels include a liquid culture medium.

In some embodiments, cells are cultured in one of any suitable culture media. Different culture media having different ranges of pH, glucose concentration, growth factors, and other supplements can be used for different cell types or for different applications. In some embodiments, custom cell culture media or commercially available cell culture media such as Dulbecco's Modified Eagle Medium, Minimum Essential Medium, RPMI medium, HA or HAT medium, or other media available from Life Technologies or other commercial sources can be used. In some embodiments, cell culture media include serum (e.g., fetal bovine serum, bovine calf serum, equine serum, porcine serum, or other serum). In some embodiments, cell culture media are serum-free. In some embodiments, cell culture media include human platelet lysate (hPL). In some embodiments, cell culture media include one or more antibiotics (e.g., actinomycin D, ampicillin, carbenicillin, cefotaxime, fosmidomycin, gentamycin, kanamycin, neomycin, penicillin, penicillin streptomycin, polymyxin B, streptomycin, tetracycline, or any other suitable antibiotic or any combination of two or more thereof). In some embodiments, cell culture media include one or more salts (e.g., balanced salts, calcium chloride, sodium chloride, potassium chloride, magnesium chloride, etc.). In some embodiments, cell culture media include sodium bicarbonate. In some embodiments, cell culture media include one or more buffers (e.g., HEPES or other suitable buffer). In some embodiments, one or more supplements are included. Non-limiting examples of supplements include reducing agents (e.g., 2-mercaptoethanol), amino acids, cholesterol supplements, vitamins, transferrin, surfactants (e.g., non-ionic surfactants), CHO supplements, primary cell supplements, yeast solutions, or any combination of two or more thereof. In some embodiments, one or more growth or differentiation factors are added to cell culture media. Growth or differentiation factors (e.g., WNT-family proteins, BMP-family proteins, IGF-family proteins, etc.) can be added individually or in combination, e.g., as a differentiation cocktail comprising different factors that bring about differentiation toward a particular lineage. Growth or differentiation factors and other aspects of a liquid media can be added using automated liquid handlers integrated as part of an incubator provided herein.

In some aspects, the incubators and methods described herein provide and maintain appropriate temperature, and gas mixtures for cell growth. It should be appreciated that cell growth conditions differ for different cell types and that the incubators described herein can be programmed to maintain different conditions. In some embodiments, conditions of approximately 37° C., and 5% $CO_2$ are used for mammalian cells.

In some embodiments, the incubators and methods described herein are used to monitor or assay the culture media for nutrient depletion, changes in pH, changes in temperature, accumulation of apoptotic or necrotic cells, and/or cell density. In some embodiments, the incubators and methods described herein are used to modify or change the culture media or conditions and/or to passage the cell cultures when appropriate. In some embodiments, these procedures are automated.

In some embodiments (e.g., for adherent cell cultures), culture media can be removed directly by aspiration and replaced with fresh media. In some embodiments (e.g., for non-adherent/suspension cultures), media changes can involve centrifuging a cell culture, removing the old culture media and replacing it with fresh media. In some embodiments, the centrifuge is located in the internal chamber of an incubator. In some embodiments, culture vessels allow for continuous media replacement. In some embodiments, the incubators described herein may include one or more components that can be used to process, replace, supply, and/or maintain different aspects of a culture media to support cells. Incubators may include a reservoir containing waste media and/or a reservoir containing fresh media. Such reservoirs may be present (e.g., for temporary storage) within a refrigerator inside the incubator or a refrigerated section of the incubator. In some embodiments, one or more reservoirs are provided outside the incubators and piping is provided into and out from the incubator space to supply or draw from a liquid handler units (e.g., liquid handle units having an aspirator) or temporary reservoir within the incubator to facilitate cells feeding, media changes, and other related needs. For suspension cells, devices may be provided within the incubator to separate cells from waste media (e.g., centrifuge(s) to facilitate cell pelleting) to facilitate automated media changes as part of an incubator provided herein. In some embodiments, the document provides a system comprising a cell culture incubator connected to a computer, capable of automatically monitoring and adjusting cell culture conditions for optimal growth of the cell culture.

In some embodiments, cells are passaged within an incubator cabinet described herein. In some embodiments, a cell culture is split and a subset of the cell culture is transferred to a fresh culture vessel for further growth. In some embodiments (e.g., for adherent cell cultures), cells are detached (e.g., mechanically, for example using gentle scraping, and/or enzymatically, for example, using trypsin-EDTA or one or more other enzymes) from a surface prior to being transferred to a fresh culture vessel. In some embodiments (e.g., for suspension cell cultures), a small volume of a cell culture is transferred to a fresh culture vessel.

In some embodiments, cell cultures are manipulated in other ways during culture within an incubator cabinet of an incubator provided herein. For example, cell cultures may be transfected with nucleic acids (e.g., DNA or RNA) or exposed to viral infection (e.g., using recombinant virus particles to deliver DNA or RNA).

Aseptic techniques can be used to prevent or minimize contamination of cell cultures during growth and manipulation. In some embodiments equipment (e.g., pipettes, fluid handling devices, manipulating devices, other automated or robotic devices, etc.) that is used for cell culture is sterilized using an appropriate technique. Non-limiting techniques include heat exposure (e.g., autoclaving), surface disinfection (e.g., using alcohol, bleach, or other disinfectant), irradiation, and/or exposure to a disinfectant gas (e.g., ozone, hydrogen peroxide, etc.) as described herein. In some embodiments, media is sterilized using an appropriate technique. Non-limiting techniques include heat exposure (e.g., autoclaving), antimicrobial/antiviral treatment, filtration, and/or irradiation.

In some embodiments, manipulations of cell cultures are performed under aseptic conditions, for example, in an environment (e.g., within an incubator chamber) that has been disinfected and in which the air has been filtered to remove potential contaminants.

In some embodiments, cell cultures are grown and maintained under GMP-compliant conditions, including those that include using GMP-compliant media or GMP-compliant liquid handling equipment. In some cases, cell cultures are grown and maintained by performing methods in conjunction with standard operation procedures (SOPs).

In some embodiments, cell cultures can be monitored and/or evaluated to detect contamination. In some embodiments, contamination by cells from a different type of organism can be detected. In some embodiments, contamination of a mammalian cell culture by mycoplasma, bacteria, yeast, or viruses can be detected using any suitable technique. In some embodiments, cell culture contamination can be detected by assaying for changes or for rates of change of one or more culture properties such as pH, turbidity, etc., that are characteristic of contamination (e.g., by bacteria or yeast) and not characteristic of the cells (e.g., mammalian cells) being grown in culture. In some embodiments, one or more molecular detection assays (e.g., PCR, ELISA, RNA labeling or other enzymatic techniques) or cell-based assays can be used to detect contamination (e.g., mycoplasma, bacterial, yeast, viral, or other contamination).

In some embodiments, cell cultures can be monitored and/or evaluated to detect contamination with cells of similar types (e.g., a human cell line contaminated by different human cells or by different mammalian cells). In some embodiments, cell cultures and their potential contamination can be evaluated using DNA sequencing or DNA fingerprinting (e.g., short tandem repeat-STR-fingerprinting), isoenzyme analysis, human lymphocyte antigen (HLA) typing, chromosomal analysis, karyotyping, cell morphology, or other.

In some embodiments, cells produced using the incubators or methods described herein can be frozen to preserve them for later use and/or for transport. In some embodiments, cells are mixed with a cryopreservation composition after growth and/or differentiation and prior to freezing. A cryopreservation composition can be added to a cell culture vessel or cells can be transferred from a cell culture vessel to a cryopreservation vessel along with a cryopreservation composition. Non-limiting examples of cryoprotectants that can be included in a cryopreservation composition include DMSO, glycerol, PEG, sucrose, trehalose, and dextrose. In some embodiments, a freezer may be provided as a component of an incubator to facilitate freezing of cells isolated from cell cultures. For example, one or more freezers may be located in an internal chamber and/or integrated into the incubator cabinet (e.g., into a wall of the incubator cabinet).

Cell Culture Incubators

This document relates to incubator and methods for culturing, manipulating, and/or monitoring cells under controlled conditions (e.g., under aseptic and/or sterile conditions). In some embodiments, the cell culture incubators provided herein include an incubator cabinet defining an internal chamber for incubation of cells in one or more cell culture vessels, in which the internal chamber is configured to hold the one or more cell culture vessels. In some cases, in addition to an internal door from the transfer chamber to the internal chamber, the incubators include at least one external door (e.g., 1, 2, 3, 4, or more external doors) opening from an external environment directly to the internal chamber, for example, to provide alternative access to the internal chamber during periods of time when the incubator is not operational, e.g., during maintenance of the incubator. In some embodiments, the incubators include a storage location within the internal chamber for storing one or more cell culture vessels.

As used herein, an "incubator cabinet" is a housing that includes one or more chambers configured to hold one or more cell culture vessels. In some embodiments, an incubator cabinet includes a transfer chamber and an internal chamber, one or both of which are configured to hold one or more cell culture vessels. In some embodiments, an incubator may include one or more other elements such as one or more gas sources (e.g., a gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., openings or panels) windows (e.g., optical windows made of glass, plastic, composite, or other substantially transparent material for viewing an area inside the incubator), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g., cameras, barcode readers), electrical elements (e.g., circuits, cables, power cords, and power supplies such as batteries, generators, and direct or alternating current supplies), computers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touch-screens). In some embodiments, one or more of these other elements are part of the incubator, but are external to the incubator cabinet. In some embodiments, one or more of these other elements are included within the incubator cabinet.

In some embodiments, incubators or incubator cabinets provided herein are rectangularly cuboidal in shape. In some embodiments incubators or incubator cabinets provided herein have a rectangular footprint in a range of 1 $ft^2$ to 16 $ft^2$. In some embodiments incubators or incubator cabinets provided herein have a rectangular footprint of up to about 1 $ft^2$, 2 $ft^2$, 3 $ft^2$, 4 $ft^2$, 5 $ft^2$, 6 $ft^2$, 7 $ft^2$, 8 $ft^2$, 9 $ft^2$, 10 $ft^2$, 11 $ft^2$, 12 $ft^2$, 13 $ft^2$, 14 $ft^2$, 15 $ft^2$, or 16 $ft^2$. In some embodiments incubators or incubator cabinets provided herein have a total chamber volume in a range of 1 $ft^3$ to 100 $ft^3$. In some embodiments incubators or incubator cabinets provided herein have a chamber volume of up to about 1 $ft^3$, 5 $ft^3$, 10 $ft^3$, 25 $ft^3$, 50 $ft^3$ or 100 $ft^3$. In some embodiments incubators or incubator cabinets provided herein have a rectangular footprint in a range of 0.09 $m^2$ to 1.78 $m^2$. In some embodiments incubators or incubator cabinets provided herein have a rectangular footprint of up to about 0.1 $m^2$, 0.2 $m^2$, 0.3 $m^2$, 0.4 $m^2$, 0.5 $m^2$, 0.6 $m^2$, 0.7 $m^2$, 0.8 $m^2$, 0.9 $m^2$, 1.0 $m^2$, 1.1 $m^2$, 1.2 $m^2$, 1.3 $m^2$, 1.4 $m^2$, 1.5 $m^2$, 1.6 $m^2$, or 1.7 $m^2$. In some embodiments, incubators or incubator cabinets provided herein have a total chamber volume in a range of 0.03 $m^3$ to 3 $m^3$. In some embodiments incubators or incubator cabinets provided herein have a chamber volume of up to about 0.03 $m^3$, 0.1 $m^3$, 0.3 $m^3$, 1 $m^3$ or 3 $m^3$.

Storage Locations

As used herein, a "storage location" refers to a location at which one or more cell culture vessels is stored (e.g., within an incubator cabinet). For example, one or more cell culture vessels may be stored at a storage location and later transferred to a different location (e.g., an imaging location). The storage location may be disposed in the internal chamber of the incubator cabinet. A storage location may be configured for storing a plurality of cell culture vessels. For example, a storage location may include one or more storage arrays, racks, shelves, pigeon-holes, cubbies, trays, slots, or other positions or mechanisms. In some embodiments, a storage location may be configured to store cell culture vessels horizontally, while in other embodiments it may be configured to store cell culture vessels vertically. For example, a storage location may include a plurality of slots to receive cell culture vessels stacked vertically over one another. A storage location may be configured to hold 1, 2, 3, 4, 5, 6, 7, 8, 9, 10, 15, 20, 25, 30, 35, 40, 45, 50, 100, or any other number of cell culture vessels. In some embodiments, a storage location may be configured to hold greater than 100 cell culture vessels. In some embodiments, a storage location may include a mechanism for moving one or more storage arrays, racks, shelves, pigeon-holes, cubbies, trays, slots, or other positions or mechanisms. For example, a storage location may include one or more motors and movable stages (e.g., an xy or xyz stage) to move a storage rack from one position in an internal chamber to another position in an internal chamber, e.g., to facilitate access to one or more cell culture vessels stored in different locations. In some embodiments, the incubator cabinet may include one or more cell culture vessel transfer devices for moving one or more cell culture vessels.

A storage location may be configured to securely hold or receive one or more cell culture vessels. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel may include one or more grooves or depressions and/or may involve pieces of molded plastic. For example, a cell culture vessel may include one or more protruded features (e.g., a rim or knob) that is molded for insertion into one or more corresponding grooves, holes, or depressions at a storage location. In some cases, a cell culture vessel may include one or more grooves, holes, or depressions that are molded to fit one or more corresponding protruded features at a storage location.

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager. In some embodiments, fiducial marks may be associated with moving parts, including transfer devices and robotics devices.

Materials

In some embodiments, an incubator cabinet is single-walled. In some embodiments, an incubator is double-walled. In some embodiments, insulation material is provided between the double walls of an incubator cabinet to control heat loss from the cabinet and facilitate temperature control in the cabinet. In some embodiments, the outer wall of an incubator cabinet includes a sheet metal, e.g., a 14-20 gauge cold rolled steel. In some embodiments, an inner wall (e.g., a chamber surface) of an incubator cabinet includes electro-polished stainless steel. In some embodiments, an inner wall (e.g., a chamber surface) of an incubator cabinet includes corrosion resistant materials, such as, titanium, cobalt-chrome, tantalum, platinum, zirconium, niobium, stainless steel, and alloys thereof. However, in some embodiments, a chamber surface of an incubator cabinet includes a polymeric material such as polytetrafluoroethylene (PTFE), or a polymeric material know under the trade name of Parylene. In some embodiments, a chamber surface may have anti-microbial properties, such as copper or silver or anti-microbial compounds incorporated into a polymeric surface coating.

Cell Assays

In certain embodiments, incubators provided herein are configured to permit one or more assays to be performed within an incubator cabinet or within a chamber operably connected to an incubator cabinet, e.g., a separate assay chamber that is part of the incubator. In some embodiments, incubators provided herein are configured to permit performance of a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, a nuclear fragmentation assay, or a combination thereof. Other exemplary assays include BrdU, EdU, or H3-thymidine incorporation assays; DNA content assays using a nucleic acid dye, such as Hoechst Dye, DAPI, actinomycin D, 7-aminoactinomycin D, or propidium iodide; cellular metabolism assays such as AlamarBlue, MTT, XTT, and CellTitre Glo; nuclear fragmentation assays; cytoplasmic histone associated DNA fragmentation assays; PARP cleavage assays; and, TUNEL staining assays.

Treatments and Experimental Interventions

In certain embodiments, incubators provided herein are configured to permit high-throughput screening (HTS) within an incubator cabinet. In some embodiments, HTS refers to testing of up to, for example, 100,000 compounds per day. In some embodiments, screening assays may be carried out in a multi-well format, for example, a 96-well, 384-well format, or 1,536-well format, and can be performed using automated protocols. In such high throughput assays, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays. Typically, HTS implementations of the assays described herein involve the use of automation. In some embodiments, an integrated robot system that includes of one or more robotic arms transports assay microplates between multiple assay stations for compound, cell, and/or reagent addition, mixing, incubation, and finally readout or detection. In some aspects, an HTS assay may include preparing, incubating, and analyzing many plates simultaneously, further speeding the data-collection process.

In some embodiments, assays can include test cells, control cells, and one or more test compounds, e.g., 10, 100, 1000, 10,000, or more test compounds. The cells and test agents can be arranged in one or more vessels in a manner suitable for assessing effect of the test compound(s) on the cells. These assays can be performed within one or more incubator cabinets of one or more incubators described herein. Typically, the vessels contain a suitable tissue culture medium, and the test compounds are present in the tissue culture medium and may be delivered to the culture medium within an incubator cabinet of an incubator provided herein in an automated fashion. A medium appropriate for culturing a particular cell type can be selected for use. In some embodiments, a medium is free or essentially free of serum or tissue extracts, while in other embodiments such a component is present. In some embodiments, cells are cultured on a plastic or glass surface.

Microscopy

In some embodiments, an incubator provided herein is configured with a microscope or other imager for purposes of monitoring cell growth, viability or other aspect of cells. In some embodiments, the microscope or imager is used in conjunction with an assay performed within an incubator cabinet, such as an image based phenotypic screen or assay.

As used herein, an "imager" refers to an imaging device for measuring light (e.g., transmitted or scattered light), color, morphology, or other detectable parameters such as a number of elements or a combination thereof. An imager may also be referred to as an imaging device. In certain embodiments, an imager includes one or more lenses, fibers, cameras (e.g., a charge-coupled device or CMOS camera), apertures, mirrors, light sources (e.g., a laser or lamp), or other optical elements. An imager may be a microscope. In some embodiments, the imager is a bright-field microscope. In other embodiments, the imager is a holographic imager or microscope. In other embodiments, the imager is a fluorescence microscope.

As used herein, a "fluorescence microscope" refers to an imaging device which is able to detect light emitted from fluorescent markers present either within and/or on the surface of cells or other biological entities, said markers emitting light at a specific wavelength in response to the absorption a light of a different wavelength.

As used herein, a "bright-field microscope" is an imager that illuminates a sample and produces an image based on the light absorbed by the sample. Any appropriate bright-field microscope may be used in combination with an incubator provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation, from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet includes a single imager. In some embodiments, an incubator cabinet includes two imagers. In some embodiments, the two imagers are the same type of imager (e.g., two holographic imagers or two bright-field microscopes). In some embodiments, the first imager is a bright-field microscope and the second imager is a holographic imager. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope.

As used herein, an "imaging location" is the location where an imager images one or more cells. For example, an imaging location may be disposed above a light source and/or in vertical alignment with one or more optical elements (e.g., lens, apertures, mirrors, objectives, and light collectors).

Modular Incubator Systems

In some embodiments, incubators described herein can be configured to form a plurality of modular workstations. Modular workstations may provide adequate processing capability for parallel cell culture, for example, each workstation performing a specific function in a protocol (e.g., a liquid handling workstation, a bright field imaging workstation, a bright field and/or fluorescent workstation, etc.). In some embodiments, workstations may also be configured for cell or stem cell colony identification and digital marking, cell manipulation, cell re-plating, and elimination of colonies, etc. In some embodiments, incubators described herein can be joined in an airtight manner (e.g., via transfer chambers each configured to connect incubator cabinets via internal doors) to form a modular complex of workstations. In some embodiments, workstations may comprise an imager, a cell culture transfer device, a manipulator, one or more storage locations, or a combination of the foregoing.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for cell culturing comprising the steps of:
   receiving a cell culture vessel from an incubator housing at a transfer device;
   moving the cell culture vessel through a door into an internal chamber having at least one imager at an imaging location therein for imaging a cell culture in the cell culture vessel under the control of a controller;
   wherein the transfer device moves the cell culture vessel into the imaging location within the internal chamber;
   imaging the cell culture in the cell culture vessel under the control of the controller; and
   moving the cell culture vessel from the imaging location and through the door of the internal chamber under the control of the controller for placement in the incubator, wherein the transfer device is positioned to receive another cell culture vessel.

2. The method according to claim 1, wherein the transfer device travels longitudinally into and out of the imaging location.

3. The method according to claim 1, wherein the at least one imager comprises three imagers.

4. The method according to claim 3, wherein the imagers are bright-field imagers.

5. The method according to claim 4, wherein image data from the imagers is transmitted to a network.

6. The method according to claim 1, further comprising producing light signals in response to the sensing of a culture vessel and wherein the controller receives the light signals to enable the controller to determine the location of the cell culture vessel moving into and out of the imaging location.

7. The method according to claim 6, wherein the light signals are communicated wirelessly to the controller.

8. The method according to claim 6, wherein the light signals detect the position of a cell culture vessel without a sensor on the cell culture vessel.

9. The method according to claim 6, wherein the light signals form a grid of light signals.

10. The method according to claim 6, wherein the light signals comprise lasers.

11. The method according to claim 10, wherein the lasers form a grid of laser light signals.

12. The method according to claim 1, wherein the cell culture vessel slides into and out of the imaging location.

* * * * *